(12) United States Patent
Kadohira et al.

(10) Patent No.: US 12,354,018 B2
(45) Date of Patent: Jul. 8, 2025

(54) PREDICTION MANAGEMENT SYSTEM, PREDICTION MANAGEMENT METHOD, DATA STRUCTURE, PREDICTION MANAGEMENT DEVICE AND PREDICTION EXECUTION DEVICE

(71) Applicant: NATIONAL INSTITUTE FOR MATERIALS SCIENCE, Tsukuba (JP)

(72) Inventors: Takuya Kadohira, Tsukuba (JP); Satoshi Minamoto, Tsukuba (JP); Makoto Watanabe, Tsukuba (JP); Masahiko Demura, Tsukuba (JP); Junya Inoue, Tokyo (JP); Manabu Enoki, Tokyo (JP)

(73) Assignee: NATIONAL INSTITUTE FOR MATERIALS SCIENCE, Tsukuba (JP)

( * ) Notice: Subject to any disclaimer, the term of this patent is extended or adjusted under 35 U.S.C. 154(b) by 1113 days.

(21) Appl. No.: 17/279,680

(22) PCT Filed: Oct. 1, 2019

(86) PCT No.: PCT/JP2019/038709
§ 371 (c)(1),
(2) Date: Mar. 25, 2021

(87) PCT Pub. No.: WO2020/075573
PCT Pub. Date: Apr. 16, 2020

(65) Prior Publication Data
US 2021/0397976 A1    Dec. 23, 2021

(30) Foreign Application Priority Data

Oct. 10, 2018    (JP) .................................. 2018-191904

(51) Int. Cl.
*G06N 5/02*    (2023.01)

(52) U.S. Cl.
CPC ...................................... *G06N 5/02* (2013.01)

(58) Field of Classification Search
CPC ........... G06F 30/20; G06F 17/50; G06N 5/02; G06Q 10/04; G06Q 10/06; G16C 60/00; G16C 20/30; G16C 20/70; Y02P 90/30
See application file for complete search history.

(56) References Cited

U.S. PATENT DOCUMENTS

2006/0190137 A1*  8/2006  Free ....................... G16C 20/70
                                                        700/266
2014/0067457 A1   3/2014  Nagendra et al.
(Continued)

FOREIGN PATENT DOCUMENTS

EP          2778990 A2    9/2014
JP        2002328961 A   11/2002
WO   WO-2004038602 A1 *  5/2004  ......... G06F 19/3437

OTHER PUBLICATIONS

Killeen, Neil EB, et al. "Integration of modern data management practice with scientific workflows." 2012 IEEE 8th International Conference on E-Science. IEEE, 2012. (Year: 2012).*
(Continued)

*Primary Examiner* — Randall K. Baldwin
(74) *Attorney, Agent, or Firm* — Hoffmann & Baron, LLP

(57) ABSTRACT

System that makes a prediction regarding a material, including: storing descriptors each describing a parameter regarding processing means, structure, property, or performance of the material; storing prediction models each describing an input and output relationship among the descriptors, wherein each prediction model inputs one of at least two of the processing means, structure, property, and performance, and outputs another one thereof; storing workflows each describing that at least two of the prediction models are connected via a descriptor, wherein the output of one prediction model is accepted as the input of another prediction model; giving
(Continued)

an input to each of the workflows, executing the workflow including execution of each prediction model included in the workflow, and storing an execution result including an output result of each prediction model included in the workflow; managing execution results, workflows, prediction models, and descriptors in four hierarchical layers by assigning a unique identifier.

10 Claims, 23 Drawing Sheets

(56) References Cited

U.S. PATENT DOCUMENTS

| | | | | |
|---|---|---|---|---|
| 2014/0236548 A1* | 8/2014 | Conduit | ............... | G16C 20/30 703/2 |
| 2018/0096267 A1* | 4/2018 | Masekera | ............ | G06Q 10/06 |
| 2018/0113967 A1 | 4/2018 | Agrawal et al. | | |
| 2018/0165604 A1 | 6/2018 | Minkin et al. | | |
| 2018/0189679 A1* | 7/2018 | Kang | ................... | G06N 5/022 |

OTHER PUBLICATIONS

Freedman, Vicky, et al. "A collaborative extensible user environment for simulation and knowledge management." 2015 International Conference on Collaboration Technologies and Systems (CTS). IEEE, 2015. (Year: 2015).*
Pham, Thanh-Phuong, Juan J. Durillo, and Thomas Fahringer. "Predicting workflow task execution time in the cloud using a two-stage machine learning approach." IEEE Transactions on Cloud Computing 8.1 (2017): 256-268. (Year: 2017)*
QuesTek Innovations LLC, Materials by Design®, https://www.questek.com/materials-by-design.html retrieved on Aug. 15, 2019.
International Search Report dated Dec. 24, 2019.
European Search Report dated Feb. 11, 2022 issued in connection with Application No. EP 19870484.3.

* cited by examiner

FIG. 2A

| DESCRIPTOR ID | ALIAS | SUMMARY | CLASSI-FICATION | DIMEN-SION | UNIT | REGISTERER | REGISTRATION DATE AND TIME | UPDATE DATE AND TIME | STRUCTURE |
|---|---|---|---|---|---|---|---|---|---|
| D0001 | STEEL STANDARD | STANDARD MODEL NUMBER | STRUC-TURE | 1 | 1 | U001 | 2018/06/01 10:00 | 2018/06/01 10:00 | /···/D0001.json |
| D0002 | COOLING RATE A | (BLANK) | PROC-ESSING | $\Theta T^{-1}$ | °C/s | U001 | 2018/06/01 10:05 | 2018/06/01 14:10 | /···/D0002.json |
| ⋮ | ⋮ | ⋮ | ⋮ | ⋮ | ⋮ | ⋮ | ⋮ | ⋮ | ⋮ |

FIG. 2B

```
{
    "$schema":"http://json-schema.org/draft-06/schema#",
    "type":"object",
    "properties":{
        "JISnumber":{
            "type":"string"
        },
        "unit":{
            "type":"string"
        }
    }
}
```

FIG. 3A

| PREDICTION MODEL ID | ALIAS | EXECUTION FORMAT | REGISTERER | REGISTRATION DATE AND TIME | UPDATE DATE AND TIME | INPUT AND OUTPUT PORT | MANAGEMENT | ... |
|---|---|---|---|---|---|---|---|---|
| M0001 | CHARPY TEST | /.../M0001.exe | U001 | 2018/07/01 10:00 | 2018/07/01 10:00 | M0001P01, M0001P02, M0001P03, M0001P04... | ○ | ... |
| ... | ... | ... | ... | ... | ... | ... | ... | ... |

FIG. 3B

| PORT ID | IDENTIFICATION | CLASSIFICATION | ESSENTIAL | DESCRIPTOR | ... |
|---|---|---|---|---|---|
| M0001P01 | INPUT | STRUCTURE | ○ | D0001 | ... |
| M0001P02 | INPUT | PROCESSING | ○ | D0002 | ... |
| M0001P03 | OUTPUT | PROPERTY | ○ | D0003 | ... |
| ... | ... | ... | ... | ... | ... |

FIG. 4A

| WORKFLOW ID | ALIAS | DESCRIPTION | REGISTERER | REGISTRATION DATE AND TIME | UPDATE DATE AND TIME | USE MODEL | ... |
|---|---|---|---|---|---|---|---|
| W0001 | PERFORMANCE TEST 1 | ○○○ | U001 | 2018/08/01 10:00 | 2018/08/01 10:00 | M0001, M0002 | ... |
| ... | ... | ... | ... | ... | ... | ... | ... |

FIG. 4B

| WORKFLOW ID | PORT ID | CONNECTING PORT | ... |
|---|---|---|---|
| W0001 | M0001P01 | M0002P02 | ... |
| W0001 | M0001P02 | INPUT | ... |
| W0001 | M0001P03 | OUTPUT | ... |
| ... | ... | ... | ... |

FIG. 5A

| RUN ID | EXECUTOR | DESCRIPTION | WORKFLOW | STATUS | EXECUTION PARAMETER | EXECUTION DATE AND TIME | COMPLETION DATE AND TIME | COMPUTATION JOB | DATA STORAGE | ... |
|---|---|---|---|---|---|---|---|---|---|---|
| R0001 | U001 | W1_01 | W0001 | COMPLETION | R0001P001, R0001P002 | 2018/08/01 10:00 | 2018/08/01 10:02 | R0001J0001, R0001J0002 | /.../R0001/ | ... |
| ... | ... | ... | ... | ... | ... | ... | ... | ... | ... | ... |

FIG. 5B

| EXECUTION PARAMETER | NAME | TYPE | ESSENTIAL | UNIT | PARAMETER | ... |
|---|---|---|---|---|---|---|
| R0001P001 | THERMAL HISTORY | File | ○ | [s, °C] | input1.json | ... |
| ... | ... | ... | ... | ... | ... | ... |

FIG. 5C

| COMPUTATION JOB | JOB NAME | CREATION DATE AND TIME | START DATE AND TIME | COMPLETION DATE AND TIME |
|---|---|---|---|---|
| R0001J0001 | PREDICTION MODEL A | 2018/08/01 10:00 | 2018/08/01 10:00 | 2018/08/01 10:00 |
| ... | ... | ... | ... | ... |

FIG. 6

```
<?xml version="1.0" encoding="UTF-8"?>
<run>
<ID>R0001</ID>
<workflow>
  <ID>W0001</ID>
  <models>
    <model>
      <ID>M0001</ID>
      <ports>
        <port>
          <ID>M0001P01</ID>
          <port_category>in</port_category>
          <descriptor>
            <ID>D0001</ID>
            <file>
              <name>input1.json</name>
              <location>/.../R0001/input1.json</location>
            </file>
          </descriptor>
          <connected_port>input</connected_port>
        </port>
        <port>
        ...
        </port>
      </ports>
    </model>
    <model>
    ...
    </model>
  </models>
</workflow>
</run>
```

| USER ID | USER NAME | DICTIONARY 1 ||| ... |
| | | ID | DICTIONARY POSITION | REGISTRATION DATE AND TIME | |
|---|---|---|---|---|---|
| U001 | USER A | D0001 | /xxx/ | 2018/06/10 10:30 | ... |
| ... | ... | ... | ... | ... | ... |

FIG. 10A

```
                                                                    D20
  DESCRIPTOR ID(URI)      http://xxx.xxx.xxx.xxx/inventory/descriptor/D0001
  ALIAS                   STEEL STANDARD
  REGISTERER              U001
  DIMENSION               1
  UNIT                    1
  DESCRIPTION             STANDARD MODEL NUMBER

REGISTRATION DATE       2018/06/01 10:00
  AND TIME

UPDATE DATE             2018/06/01 10:00
  AND TIME

STRUCTURE               D0001.json  —L21

INCORPORATED            U001/xxx/
  DICTIONARY                                                     BT23

MODEL                   PREDICTION MODEL 1 —L22              [ EDIT ]
```

FIG. 10B

```
                                                                    D24
  DESCRIPTOR ID(URI)   http://xxx.xxx.xxx.xxx/inventory/descriptor/D0001
  ALIAS                [ STEEL STANDARD                    ]

DIMENSION            [ 1                                 ]
  UNIT                 [ 1                                 ]  TB25
  DESCRIPTION          [ STANDARD MODEL NUMBER             ]

STRUCTURE            [ D0001.json                        ]

BT26      BT27
                                                  [UPDATE]  [CANCEL]
```

FIG. 12B

```
PREDICTION MODEL ID(URI)   http://xxx.xxx.xxx.xxx/inventory/prediction-models/M001
ALIAS                      CHARPY TEST
CORRESPONDING PROGRAM      M001.exe
```

— TB35

INPUT DESCRIPTOR — TB36

| STEEL STANDARD | STRUCTURE (ESSENTIAL) |
| COOLING RATE A | PROCESSING (ESSENTIAL) |

OUTPUT DESCRIPTOR — TB37

| CHARPY IMPACT VALUE | PROPERTY (ESSENTIAL) |
| TRANSITION TEMPERATURE | PROPERTY (ESSENTIAL) |
| YIELD POINT | PROPERTY |
| TENSILE STRENGTH | PROPERTY |
| EXTENSION | PROPERTY |
| CROSS-SECTIONAL SHRINKAGE RATIO | PROPERTY |
| YIELD RATIO | PROPERTY |

APPLY — BT38    CANCEL — BT39

| | No. | RUN ID | WORKFLOW NAME | EXECUTOR NAME | EXECUTION DATE AND TIME | STATUS | DESCRIPTION |
|---|---|---|---|---|---|---|---|
| ☐ | 1 | R003 | PERFORMANCE TEST 1 | U001 | 18/08/02 12:00 | CANCEL | W1_03 |
| ☐ | 2 | R002 | PERFORMANCE TEST 1 | U001 | 18/08/02 11:00 | COMPLETION | W1_02 |
| ☐ | 3 | R001 | PERFORMANCE TEST 1 | U001 | 18/08/02 10:00 | COMPLETION | W1_01 |
| ... | ... | ... | ... | ... | ... | ... | ... |

RUN LIST — D50
BT52: CANCEL SELECTED RUN
BT53: DELETE SELECTED RUN
CB51, L54, D55

FIG. 17

| R001 | | | | | | CONFIRM EXECUTION STATUS | CANCEL EXECUTION | DELETE | ~D60 |
|---|---|---|---|---|---|---|---|---|---|
| | | | | | | BT61 | BT62 | BT63 | |

RUN ID               R001
WORKFLOW NAME        PERFORMANCE TEST 1 ~L64
FILE NAME            W0001.wf
EXECUTOR             U001
STATUS               COMPLETION
DESCRIPTION          W1_01

EXECUTION PARAMETER

| NAME | ESSENTIAL | TYPE | UNIT | PARAMETER |
|---|---|---|---|---|
| 1 THERMAL HISTORY | ESSENTIAL | file | | input1.json |
| 2 STEEL STANDARD | ESSENTIAL | file | | input2.json |

EXECUTION DATE AND TIME    18/08/02 10:00
COMPLETION DATE AND TIME   18/08/02 10:02

COMPUTATION JOB

| JOB NAME | CREATION DATE AND TIME | START DATE AND TIME | COMPLETION DATE AND TIME |
|---|---|---|---|
| 1 DERIVATION MODULE A | 18/08/02 10:00 | 18/08/02 10:00 | 18/08/02 10:00 |
| 2 CHARPY TEST | 18/08/02 10:01 | 18/08/02 10:01 | 18/08/02 10:02 |

EXECUTION RESULT    [DOWNLOAD]~BT65

LOG    detail.log ~L66

PREDICTION MANAGEMENT SYSTEM, PREDICTION MANAGEMENT METHOD, DATA STRUCTURE, PREDICTION MANAGEMENT DEVICE AND PREDICTION EXECUTION DEVICE

CROSS-REFERENCE TO RELATED APPLICATIONS

This application is the U.S. National Phase Application of International Application No. PCT/JP2019/038709, filed on Oct. 1, 2019, and asserts priority to Japanese Patent Application No. 2018-191904 filed on Oct. 10, 2018, all of which are hereby incorporated by reference herein in their entirety for all purposes.

TECHNICAL FIELD

The present invention relates to a prediction management system, a prediction management method, a data structure, a prediction management device, and a prediction execution device.

BACKGROUND ART

In recent years, it has been disclosed that it is important to clarify, as points of material development, four points with respect to a target material: property appearing in the material (property); a structure for achieving the property (structure); and processing means that is means for obtaining the structure and includes components of the material used for that means (processing, hereinafter including the components of the material); and performance exhibited according to the applied point (performance) (see, for example, Non-Patent Document 1).

CITATION LIST

Non-Patent Document

[Non-Patent Document 1] "Materials by Design", [online], QuestTek Innovations LLC, [Searched on Aug. 15, 2018], Internet <URL: www.questek.com/materials-by-design.html>

SUMMARY OF THE INVENTION

Problems to be Solved by the Invention

In order to clarify the above points, Non-Patent Document 1 discloses a method for clarifying the structure from the processing means, the property from the structure, and the performance from the property, sequentially. However, there has been a problem that there is no method for predicting an unexplained point by freely combining the past findings on the above points.

One aspect of the present invention has been made to solve the above problem, and an object thereof is to provide a general-purpose description, storage, and utilization method of information for realizing model construction, and to enable predictions of performances, properties, and structures of materials by freely combining the processing means, the structure, the property, and the performance of each material.

Means for Solving the Problems

One aspect of the present invention is made to solve the above-described problem, and one aspect of the present invention is a prediction management system that makes a prediction regarding a material, the prediction management system comprising: a descriptor storage unit that stores descriptors each describing a parameter regarding processing means, a structure, a property, or a performance of the material; a prediction model storage unit that stores prediction models each describing an input and output relationship among the descriptors, wherein each prediction model accepts, as an input, one of at least two of the processing means, the structure, the property, and the performance, and outputs another one thereof; a workflow storage unit that stores workflows each describing that at least two of the prediction models are connected to each other via the descriptor, wherein an output of one prediction model is accepted as an input of another prediction model; an execution unit that gives an input to each of the workflows, executes the workflow, and stores an execution result including an output result of each prediction model included in the workflow; and a processing unit that manages the execution results, the workflows, the prediction models, and the descriptors in four hierarchical layers by assigning a unique identifier.

Further, the prediction management system according to one aspect of the present invention further comprises: a registration processing unit that registers the descriptors and the prediction models; a designing unit that generates images representing the prediction models registered by the registration processing unit and designs the workflows based on a user operation of connecting a plurality of the images of the prediction models to one another; a processing unit that manages the workflows so as to be available to a plurality of users; and an execution unit that causes the execution result of the workflow to be stored including identification information of a user who executed the workflow.

Further, in the prediction management system according to one aspect of the present invention, at least one of the prediction models describes the input and output relationship among the descriptors as a plurality of types of inputs or outputs among the processing means, the structure, the property, and the performance, and the execution unit gives an input to, and executes, the workflow including the prediction model describing the input and output relationship as the plurality of types of inputs or outputs.

Further, in the prediction management system according to one aspect of the present invention, at least one of the prediction models describes the input and output relationship among the descriptors so as to accept the processing means and the structure as inputs and output the property, and the execution unit gives an input to, and executes, the workflow including the prediction model describing the input and output relationship so as to accept the processing means and the structure as inputs and output the property.

Further, in the prediction management system according to one aspect of the present invention, at least one of the prediction models describes the input and output relationship among the descriptors so as to accept the processing means and the structure as inputs and output the structure, and the execution unit gives an input to, and executes, the workflow including the prediction model describing the input and output relationship so as to accept the processing means and the structure as inputs and output the structure.

Further, one aspect of the present invention is a prediction management method in a prediction management system that makes a prediction regarding a material, the prediction management method comprising: a descriptor storage step of storing descriptors each describing a parameter regarding processing means, a structure, a property, or a performance of the material; a prediction model storage step of storing prediction models each describing an input and output relationship among the descriptors, wherein each prediction model accepts, as an input, one of at least two of the processing means, the structure, the property, and the performance, and outputs another one thereof; a workflow storage step of storing workflows each describing that at least two of the prediction models are connected to each other via the descriptor, wherein an output of one prediction model is accepted as an input of another prediction model; an execution step of giving an input to each of the workflows, executing the workflow, and storing an execution result including an output result of each prediction model included in the workflow; and a processing step of managing the execution results, the workflows, the prediction models, and the descriptors in four hierarchical layers by assigning a unique identifier.

Further, one aspect of the present invention is a data structure of data stored in a prediction management system that makes a prediction regarding a material, the data structure comprising: descriptors each describing a parameter regarding processing means, a structure, a property, or a performance of the material; prediction models each describing an input and output relationship among the descriptors, wherein each prediction model accepts, as an input, one of at least two of the processing means, the structure, the property, and the performance, and outputs another one thereof, workflows each describing that at least two of the prediction models are connected to each other via the descriptor, wherein an output of one prediction model is accepted as an input of another prediction model; and execution results of giving an input to, and executing, each of the workflows, the execution results each including an output result of each prediction model included in the workflow, wherein a unique identifier is assigned to the execution results, the workflows, the prediction models, and the descriptors in four hierarchical layers.

Further, one aspect of the present invention is a prediction management device that makes a prediction regarding a material, the prediction management device comprising: a processing unit that manages execution results, workflows, prediction models, and descriptors in four hierarchical layers by assigning a unique identifier, wherein: the descriptors each describes a parameter regarding processing means, a structure, a property, or a performance of the material; the prediction models each describes an input and output relationship among the descriptors, wherein each prediction model accepts, as an input, one of at least two of the processing means, the structure, the property, and the performance, and outputs another one thereof; the workflows each describes that at least two of the prediction models are connected to each other via the descriptor, wherein an output of one prediction model is accepted as an input of another prediction model; and the execution results are results of giving an input to, and executing, each of the workflows, and the execution results each includes an output result of each prediction model included in the workflow.

Further, one aspect of the present invention is a prediction execution device that makes a prediction regarding a material, the prediction execution device comprising: an execution unit that reads from one or more storage units, descriptors each describing a parameter regarding processing means, a structure, a property, or a performance of the material, prediction models each describing an input and output relationship among the descriptors, wherein each prediction model accepts, as an input, one of at least two of the processing means, the structure, the property, and the performance, and outputs another one thereof; and workflows each describing that at least two of the prediction models are connected to each other via the descriptor, wherein an output of one prediction model is accepted as an input of another prediction model, wherein the execution unit causes the one or more storage units to store execution results of giving an input to, and executing, each of the workflows, the execution results each including an output result of each prediction model included in the workflow.

Effects of the Invention

According to one aspect of the present invention, it is possible to provide a general-purpose description, storage, and utilization method of information for realizing model construction, and to enable predictions of performances, properties, and structures of materials by freely combining the processing means, the structure, the property, and the performance of each material.

BRIEF DESCRIPTION OF THE DRAWINGS

FIG. 2A is a diagram showing a data example of a descriptor storage unit according to the present embodiment.

FIG. 2B is a diagram showing a data example of a descriptor storage unit according to the present embodiment.

FIG. 3A is a diagram showing a data example of a prediction model storage unit according to the present embodiment.

FIG. 3B is a diagram showing a data example of the prediction model storage unit according to the present embodiment.

FIG. 4A is a diagram showing a data example of a workflow storage unit according to the present embodiment.

FIG. 4B is a diagram showing a data example of the workflow storage unit according to the present embodiment.

FIG. 5A is a diagram showing a data example of a computation result storage unit according to the present embodiment.

FIG. 5B is a diagram showing a data example of the computation result storage unit according to the present embodiment.

FIG. 5C is a diagram showing a data example of the computation result storage unit according to the present embodiment.

FIG. 6 is a diagram showing a data example of a relationship information storage unit according to the present embodiment.

FIG. 10A is a diagram showing an example of a web page displayed when browsing detailed information of the descriptor according to the present embodiment.

FIG. 10B is a diagram showing an example of a web page displayed when editing the detailed information of the descriptor according to the present embodiment.

FIG. 12B is a diagram showing an example of a web page displayed when editing the detailed information of the prediction model according to the present embodiment.

FIG. 16 is a diagram showing an example of a computation list screen in the workflow execution system according to the present embodiment.

FIG. 17 is a diagram showing an example of a computation detail screen in the workflow execution system according to the present embodiment.

MODE FOR CARRYING OUT THE INVENTION

Hereinafter, a prediction management system according to an embodiment of the present invention will be described with reference to the drawings.

Embodiment

Figure 1:
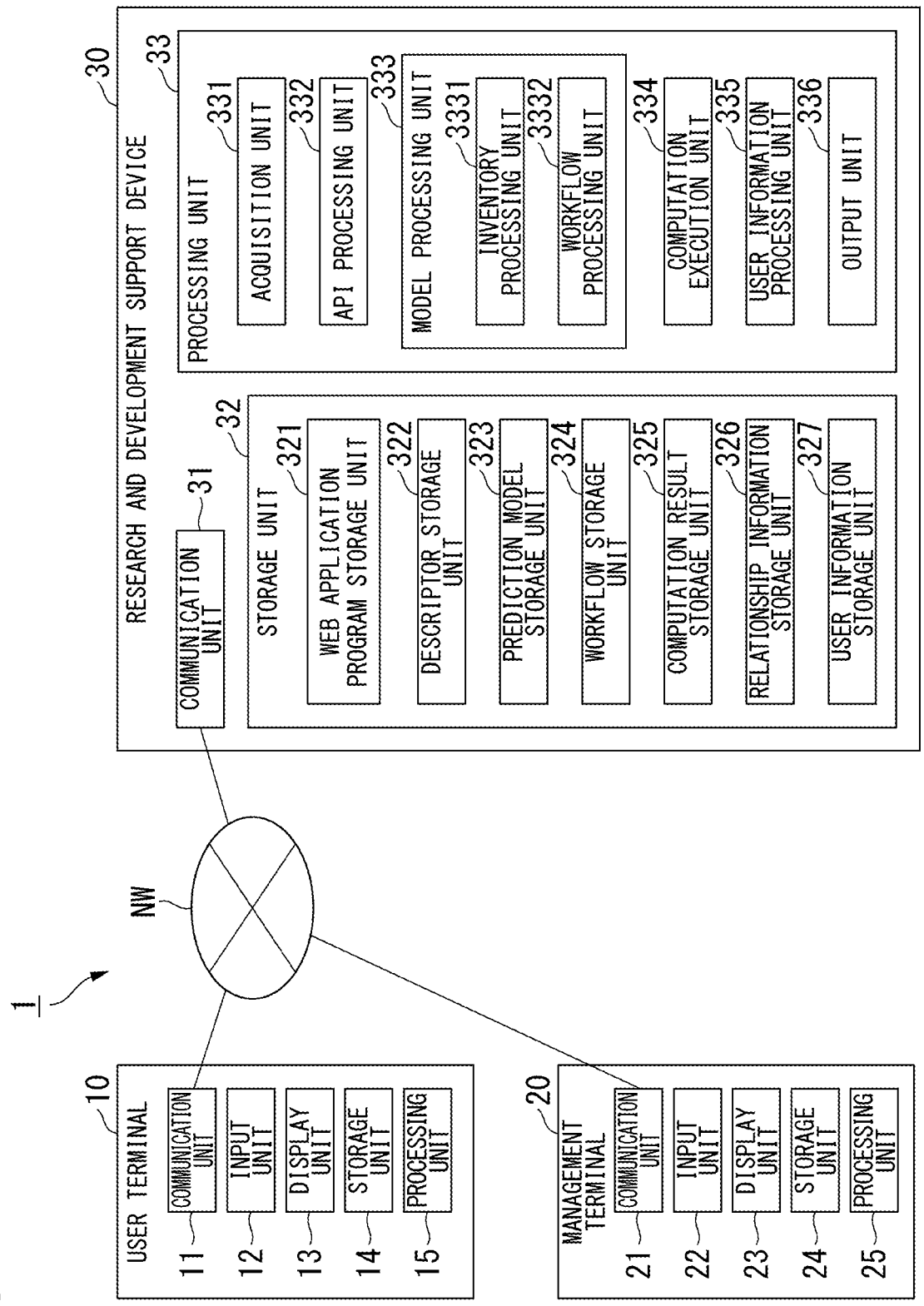
FIG. 1 is a block diagram showing an example of a prediction management system according to the present embodiment.

FIG. 1 is a block diagram showing an example of a prediction management system 1 according to the present embodiment. As shown in FIG. 1, the prediction management system 1 includes a user terminal 10, a management terminal 20, and a research and development support device 30.

Here, in the present embodiment, for convenience of explanation, an example in which the prediction management system 1 includes one user terminal 10 and one management terminal 20 will be described, but a plurality of user terminals and a plurality of management terminals may be included.

Additionally, the user terminal 10, the management terminal 20, and the research and development support device 30 are connected via a network NW.

Further, the prediction management system 1 is a system that performs, among the devices, transmission and reception of information regarding model construction for performing, for example, performance prediction, property prediction, and structure prediction of materials.

The network NW is an information and communication network including, for example, a mobile phone network, a PHS (Personal Handy-phone System) network, a VPN (Virtual Private Network) network, a dedicated communication line network, a WAN (Wide Area Network), a LAN (Local Area Network), a PSTN (Public Switched Telephone Network), or the like, or is a combination of these networks.

The user terminal 10 is a terminal device such as a personal computer, a tablet, a smartphone, or a television, for example. The user terminal 10 can be connected to the research and development support device 30 via the network NW. Further, the user terminal 10 transmits to the research and development support device 30 via the network NW, information regarding model construction for performing performance prediction, property prediction, or structure prediction of materials, which is inputted to the user terminal 10. Further, the user terminal 10 transmits to the research and development support device 30 via the network NW, information regarding data used for performing computations using the constructed model, which is inputted to the user terminal 10. Further, the user terminal 10 receives from the research and development support device 30 via the network NW, information regarding web application for performing the above-described model construction and information regarding model construction, which are stored in the research and development support device 30. Further, the user terminal 10 receives computation results with respect to the transmitted data from the research and development support device 30 via the network NW.

The user terminal 10 performs the above-described transmission and reception of information to and from the research and development support device 30 by using, for example, a UA (User Agent) such as a web browser stored in the storage unit 14. The user terminal 10 receives from the research and development support device 30 via the network NW, information regarding the transmission and reception to and from the research and development support device 30. The user terminal 10 performs transmission and reception of information to and from the research and development support device 30 by using the received information regarding the transmission and reception. Hereinafter, a description will be given with respect to an example in which the transmission and reception of information between the user terminal 10 and the research and development support device 30 is performed by using HTTP (Hypertext Transfer Protocol) via a web browser. However, the present invention is not limited thereto, and for example, a dedicated application program or a dedicated communication protocol may be used for the transmission and reception of information.

The user terminal 10 includes a communication unit 11, an input unit 12, a display unit 13, a storage unit 14, and a processing unit 15.

The communication unit 11 connects to the network NW using wired LAN communication, wireless LAN communication, or the like, and performs various communications via the network NW. The communication unit 11 connects to the research and development support device 30 via, for example, the network NW, and performs various communications with the research and development support device 30.

The input unit 12 is an input device such as a keyboard, a mouse, or a touch panel, for example. The input unit 12 receives user input information such as information regarding model construction for performing performance prediction, property prediction, and structure prediction of a material, and information for performing computations using the constructed model. The input unit 12 outputs the received user input information to the processing unit 15.

The display unit 13 includes a display device. The display device includes, for example, an organic electroluminescence display (OLED: Organic Electro-luminescence Display), a liquid crystal display (LCD: Liquid Crystal Display), or the like. The display unit 13 displays, for example, display information transmitted by display data inputted from the processing unit 15. The display unit 13 displays various information such as various operation screens and information input screens. Here, the display unit 13 may be formed as a touch panel having the function of the input unit 12.

The storage unit 14 includes, for example, an HDD (Hard Disk Drive), a flash memory, an EEPROM (Electrically Erasable Programmable Read Only Memory), a ROM (Read Only Memory), a RAM (Random Access Memory) program, or the like. The storage unit 14 stores various programs such as firmware and application programs to be executed by a CPU included in the user terminal 10, results of processing executed by the CPU, and the like. The user terminal 10 functions by, for example, the CPU included in the user terminal 10 executing the programs stored in the user terminal 10.

The processing unit 15 is a processor including a CPU (Central Processing Unit) or the like, and performs comprehensive control processing of the user terminal 10. The processing unit 15 receives from the research and development support device 30 via the communication unit 11, for example, information regarding a web application used for the model construction and displays the received information on the display unit 13. Further, the processing unit 15 receives from the research and development support device 30 via the communication unit 11, for example, information necessary for performing the model construction on the web application, and displays the received information on the display unit 13. Further, the processing unit 15 transmits to the research and development support device 30 via the communication unit 11, information for preforming the model construction, which is inputted from the input unit 12.

The management terminal 20 is a terminal device such as a personal computer, a tablet, a smartphone, a television, or the like, for example. The management terminal 20 can be connected to the research and development support device 30 via the network NW. Further, the management terminal 20 manages information regarding prediction models among the above-described information regarding the model construction.

Here, a prediction model is information describing an input and output relationship of an execution program that performs computations using, as inputs and outputs, descriptors that describe information regarding parameters regarding processing means, structures, properties, and performances of materials. The descriptor and the prediction model will be described later.

The management terminal 20 receives from the research and development support device 30 via the network NW, information regarding the prediction model for which registration application has been made. Here, the prediction model for which registration application has been made indicates a prediction model newly created by the user terminal 10. The management terminal 20 transmits to the research and development support device 30 via the network NW, information regarding a setting of the newly created prediction model, based on the received information regarding the prediction model. Here, the information regarding the setting of the prediction model is information for the newly created prediction model to be available on the web application used when the prediction model executes the model construction. The management terminal 20 transmits to the research and development support device 30 via the network NW, information for adding the information regarding the newly created prediction model to the setting information of the web application. Further, the management terminal 20 transmits to the research and development support device 30 via the network NW, information for deploying the execution program corresponding to the newly created prediction model in a predetermined directory of a storage unit 32 of the research and development support device 30 according to a predetermined rule.

The management terminal 20 performs the above-described transmission and reception of information to and from the research and development support device 30 by using, for example, a UA such as a web browser stored in the storage unit 24. The management terminal 20 receives from the research and development support device 30 via the network NW, information regarding the transmission and reception to and from the research and development support device 30. The management terminal 20 performs the transmission and reception of information to and from the research and development support device 30 by using the received information regarding the transmission and reception. Hereinafter, a description will be given with respect to an example in which the transmission and reception of information between the management terminal 20 and the research and development support device 30 is performed using HTTP via a web browser, but the example is not limited thereto. For example, a dedicated application program or a dedicated communication protocol may be used.

The management terminal 20 includes a communication unit 21, an input unit 22, a display unit 23, a storage unit 24, and a processing unit 25.

The communication unit 21 connects to the network NW using wired LAN communication, wireless LAN communication, or the like, and performs various communications via the network NW. For example, the communication unit 21 connects to the research and development support device 30 via the network NW, and performs various communications with the research and development support device 30.

The input unit 22 is an input device such as a keyboard, a mouse, or a touch panel, for example. The input unit 22 receives user input information such as information regarding the setting of the prediction model that has been changed. The input unit 22 outputs the user input information to the processing unit 25.

The display unit 23 includes a display device. The display device is, for example, an organic electroluminescence display (OLED), a liquid crystal display (LCD), or the like. The display unit 23 displays display information transferred by, for example, display data input from the processing unit 25. The display unit 23 displays various information such as various operation screens and information input screens, for example. Here, the display unit 23 may be formed as a touch panel having the function of the input unit 22.

The storage unit 24 includes, for example, an HDD, a flash memory, an EEPROM, a ROM, a RAM, or the like, and stores various programs such as firmware and application programs to be executed by the CPU included in the management terminal 20, and results of processing executed by the CPU. The management terminal 20 functions by, for example, the CPU included in the management terminal 20 executing a program stored in the management terminal 20.

The processing unit 25 is a processor including a CPU and the like, and performs comprehensive control processing of the management terminal 20. For example, the processing unit 25 receives from the research and development support device 30 via the communication unit 21, information regarding the prediction model for which registration application has been made, and displays the information on the display unit 23. Further, the processing unit 25 transmits to the research and development support device 30 via the communication unit 21, the information regarding the setting of the newly created prediction model, which is inputted from the input unit 22.

The research and development support device 30 (an example of a prediction management device) is, for example, a server device. The research and development support device 30 includes, for example, a CPU and a storage device. The research and development support device 30 is connectable to the user terminal 10 and the management terminal 20 via the network NW.

The research and development support device 30 transmits to the user terminal 10 via the network NW, information regarding the web application which is the information for executing the model construction for performing the performance prediction, the property prediction, or the structure prediction of materials. Further, the research and development support device 30 receives from the user terminal 10 via the network NW, information for performing the model construction described above, which is the information inputted to the user terminal 10. The research and development support device 30 stores in the storage unit 32, the information regarding the model construction received from the user terminal 10.

Further, the research and development support device 30 receives from the user terminal 10 via the network NW, information regarding data for performing computations using the constructed model. Further, the research and development support device 30 performs computations of the constructed models, using the received data for performing the computations. Further, the research and development support device 30 transmits to the user terminal 10 via the network NW, information regarding results of the computations performed using the received data.

The research and development support device 30 transmits to the management terminal 20 via the network NW, information regarding the prediction model for which registration application has been newly made. Further, the research and development support device 30 receives from the management terminal 20 via the network NW, the information regarding the setting of the prediction model, which is inputted to the management terminal 20 based on the transmitted information regarding the prediction model. Based on the received information, the research and development support device 30 performs a process for enabling the prediction model for which registration application has been made to be available on the web application used when executing the model construction. Further, based on the information received from the management terminal 20, the research and development support device 30 deploys an execution program corresponding to the newly created prediction model in a predetermined directory of the storage unit 32, according to a predetermined rule.

The research and development support device 30 includes a communication unit 31, a storage unit 32, and a processing unit 33.

The communication unit 31 connects to the network NW using wired LAN communication, wireless LAN communication, or the like, and performs various communications via the network NW. For example, the communication unit 31 connects to the user terminal 10 and the management terminal 20 via the network NW, and performs various communications with the user terminal 10 or the management terminal 20.

The storage unit 32 stores various information used by the research and development support device 30. The storage unit 32 includes, for example, a web application program storage unit 321, a descriptor storage unit 322, a prediction model storage unit 323, a workflow storage unit 324, a computation result storage unit 325, a relationship information storage unit 326, and a user information storage unit 327.

The web application program storage unit 321 stores, for example, information regarding a web application program necessary for the user terminal 10 to perform work regarding the model construction. The web application program storage unit 321 stores, for example, information regarding an inventory system that is an application program for executing processing regarding descriptors and prediction models described later, information regarding a workflow design system that is an application program for designing a workflow described later, information regarding a workflow execution system that is an application program for executing computations using the created workflow, and the like. Further, the web application program storage unit 321 stores information for displaying various information regarding the web application program on the UAs of the user terminal 10 and the management terminal 20.

Further, the web application program storage unit 321 stores information regarding an API (Application Programming Interface) used for transmission and reception of information to and from the user terminal 10 and the management terminal 20. Here, the API used for the transmission and reception is, for example, an API using HTTP (Hypertext Transfer Protocol), which is based on the principle of REST (REpresentational State Transfer) (RESTfull webAPI). Hereinafter, a description will be given with respect to an example in which the user terminal 10, the management terminal 20, and the research and development support device 30 perform transmission and reception of information using the REST API, but the example is not limited thereto. For example, other APIs may be used.

The descriptor storage unit 322 (an example of a descriptor database) stores information regarding descriptors. Here, a descriptor describes information regarding parameters regarding at least one of processing means, a structure, a property, and a performance of a material. For example, the descriptor storage unit 322 stores information regarding the descriptors, as shown in FIG. 2A. Further, the descriptor storage unit 322 stores information regarding a data structure accepted by the descriptor when performing computations using the constructed model, for example, as shown in FIG. 2B.

FIGS. 2A and 2B are diagrams showing a data example of the descriptor storage unit 322 according to the present embodiment.

FIG. 2A shows a data example of the information regarding the descriptors stored in the descriptor storage unit 322.

As shown in FIG. 2A, the descriptor storage unit 322 stores a "descriptor ID", an "alias", a "summary", a "classification", a "dimension", a "unit", and a "registerer", a "registration date and time", a "update date and time", and a "structure" in association with one another.

Here, the "descriptor ID" indicates identification information (an example of a unique identifier) for identifying a descriptor. The descriptor ID may be an ID whose notation is unified together with a prediction model ID, a workflow ID, a run ID, and the like, which will be described later. In this case, for example, a UUID (Universally Unique Identifier) may be used as the notation. Further, as the descriptor ID, a later-described URI (Uniform Resource Identifier) that presents information of the descriptor ID may be used. In this case, the URI in which the descriptor ID identifying each descriptor is added after a common address indicating the directory that stores the descriptor is used as the descriptor ID. Hereinafter, likewise, for the prediction model ID, the workflow ID, and the run ID, URIs that present the respective information may be used as the respective IDs.

Further, the "alias" is an alias that can specify a descriptor, and indicates an alias other than the descriptor ID. Further, the "summary" indicates information that describes a descriptor, such as information that the descriptor accepts. The "alias" and "summary" may be the same.

The "classification" indicates information regarding which parameter of the processing means, the structure, the property, or the performance of the material the descriptor is. The descriptor classified into the processing means is a description format that describes information regarding a material used in the process of processing the material and a physical quantity added, such as an amount of heat input, a heat history, a base welding material and the chemical composition of a welding material. Here, the material used in the process of the processing also includes information regarding a material component that is a component of the material.

The descriptor classified into the structure is a description format that describes information regarding a structure of the material, such as a shape of a welding portion, a statistical structural parameter of a polycrystalline such as an average particle size of the material composed of the polycrystalline, and a microstructure of the welding portion.

The descriptor classified into the property is a description format that describes information regarding property, which is a measurable behavior, independent of the amount of material, such as tensile, elongation, a yield point, a Young's modulus, a cross-sectional shrinkage ratio, a yield ratio, and a strength property value such as a Charpy impact value.

The descriptor classified into the performance is a description format that describes information regarding the performance, which is the ability to be exerted depending on where the material is applied, such as the number of stresses applied before a test piece breaks.

The "dimension" indicates the dimension of data accepted by the descriptor when executing computations, expressed using the method defined in the International System of Quantities. Further, the "unit" indicates a unit of data accepted by the descriptor when executing computations. Further, the "registerer" indicates information that identifies a user who registered the descriptor. Further, the "registration date and time" indicates the date and time when the descriptor was newly registered. Further, the "update date and time" indicates the date and time when the descriptor was recently updated. If the descriptor has not been updated after it was newly registered, the "registration date and time" and "update date and time" may be the same information, and information indicating that the update has not been made may be displayed as the "update date and time". Further, the "structure" indicates information indicating a location of a file indicating the data structure accepted by the descriptor when executing computations.

An example shown in FIG. 2A indicates that, the "alias" corresponding to the "descriptor ID" of "D0001" is "steel standard", the "summary" is "standard model number", and the "classification" is "structure". Further, it is indicated that the "dimension" is "1", the "unit" is "1", and the information accepted by the descriptor indicates that there is no unit (a dimensionless quantity such as an angle, or there is no unit such as a character string). Further, it is indicated that the "registerer" is "U001", the "registration date and time" is "2018/06/01 10:00", the "update date and time" is "2018/06/01 10:00", and that the descriptor has not been updated after the registration. Further, it is indicated that the "structure" is "/ . . . /D0001.json".

FIG. 2B shows a data example of information regarding the data structure accepted by the descriptor, which is stored in the descriptor storage unit 322. The information shown in FIG. 2B is the information described in the file (/ . . . /D0001.json) indicated by the "structure" in FIG. 2A. Here, an example is shown in which a data file accepted by the descriptor is described in JSON (JavaScript (registered trademark) Object Notification) format, and a data structure in the data file accepted by the descriptor is described in JSON Schema format, but the example is not limited thereto.

The example shown in FIG. 2B indicates that the data structure of the data file accepted by the descriptor is a structure in which the model number and the unit of the steel standard are sequentially described in the form of character string. When the format of the data accepted by the descriptor is the format shown in FIG. 2B, for example, the data expressed as {"JISnumber": "SCM435", "unit": "1"} is acceptable in executing the computations.

The prediction model storage unit 323 (an example of a prediction model database) stores information regarding prediction models. Here, the prediction model is a description of an input and output relationship of the execution program that executes the computations, which is extracted when data is actually given. The input and output of the execution program refers to data described in a descriptor, which is inputted or outputted via an input port or an output port indicating the type of data to be inputted or outputted. The type of input and output data indicated by the input and output port is selected by a user input from a predefined list at the time of designing the prediction model. Here, the predefined list includes, but is not limited to, the "processing means", the "structure", the "property", and the "performance" as standard. The classification of descriptors inputted and outputted via the input and output port must include the type of data indicated by that port. For example, when the types of descriptors are the "processing means" and the "structure", the ports to which those descriptors can be inputted and outputted are limited to the ports classified into the "processing means" or the "structure".

The prediction model storage unit 323 stores information regarding the prediction models, for example, as shown in FIG. 3A. Further, the prediction model storage unit 323 stores information regarding the input and output port included in the prediction model, for example, as shown in FIG. 3B.

FIGS. 3A and 3B are diagrams showing a data example of the prediction model storage unit 323 according to the present embodiment.

FIG. 3A shows a data example of the information regarding the prediction models stored in the prediction model storage unit 323. As shown in FIG. 3A, the prediction model storage unit 323 stores a "prediction model ID", an "alias", an "execution format", a "registerer", a "registration date and time", an "update date and time", an "input and output port", and "management" in association with one another.

Here, the "prediction model ID" indicates identification information (an example of a unique identifier) for identifying a prediction model. Further, the "alias" indicates an alias other than the prediction model ID, which can specify a prediction model. Further, the "execution format" indicates information regarding a directory in which the execution program corresponding to the prediction model is deployed. Further, the "registration date and time" indicates the date and time when the prediction model was newly registered. Further, the "update date and time" indicates the date and time when the prediction model was recently updated. If the prediction model has not been updated after it was newly registered, the "registration date and time" and the "update date and time" may be the same information, or information indicating that the update has not been made may be displayed as the "update date and time". Further, the "input and output port" indicates information that identifies the input port and the output port included in the prediction model. Further, the "management" indicates information that identifies whether or not processing regarding registration has been performed by a user (administrator) of the management terminal 20 when the prediction model is registered for the first time.

The example shown in FIG. 3A indicates that the "alias" corresponding to the "prediction model ID" of "M0001" is "Charpy test", the "execution format" is "/ . . . /M0001.exe", and the "registerer" is "U001", the "registration date and time" is "2018/07/01 10:00", and the "update date and time" is "2018/07/01 10:00", and indicates that it is the prediction model that has not been updated after the registration. Further, it is indicated that the "input and output port" is "M0001P01, M0001P02, M0001P03, M0001P04 . . . ", and that a plurality of input and output ports are present in the prediction model. Further, it is indicated that the "management" is "o" which indicates that the administrator has performed the processing regarding the registration.

FIG. 3B shows a data example of information regarding the input and output ports of the prediction models stored in the prediction model storage unit 323. As shown in FIG. 3B, the prediction model storage unit 323 stores a "port ID", an "identification", a "classification", "essential", and a "descriptor" in association with one another.

Here, the "port ID" indicates identification information for identifying an input and output port of a prediction model. Further, the "identification" indicates information for identifying whether the port is an input port or an output port. Further, the "classification" indicates the type of data accepted by the input and output port. Further, the "essential" indicates whether or not data is always inputted and outputted to and from the port. Further, the "descriptor" indicates a descriptor ID of a descriptor inputted and outputted to and from the port.

The example shown in FIG. 3B indicates that the "identification" corresponding to the "port ID" of "M0001P01" is "input", the "classification" is "structure", the "essential" is "o", and the "descriptor" is "D0001", and indicates that the port indicated by "M0001P01" is an input port that must accept the descriptor classified into the structure, and the descriptor ID of "D0001" is specified as the descriptor to be accepted.

The workflow storage unit 324 (an example of a workflow database) stores information regarding workflows. Here, a workflow is a description of a plurality of prediction models connected to one another via input and output descriptors.

The workflow storage unit 324 stores information regarding the workflows, for example, as shown in FIG. 4A. Further, the workflow storage unit 324 stores information regarding connection relationships among a plurality of prediction models included in the workflows, for example, as shown in FIG. 4B.

FIGS. 4A and 4B are diagrams showing a data example of the workflow storage unit 324 according to the present embodiment.

FIG. 4A shows a data example of information regarding the workflows stored in the workflow storage unit 324. As shown in FIG. 4A, the workflow storage unit 324 stores a "workflow ID", an "alias", an "description", a "registerer", a "registration date and time", an "update date and time", and a "use model" in association with one another.

Here, the "workflow ID" indicates identification information (an example of a unique identifier) for identifying a workflow. Further, the "alias" indicates an alias other than the workflow ID, which can specify the workflow. Further, the "description" indicates information for describing the workflow. Further, the "registration date and time" indicates the date and time when the workflow was newly registered. Further, the "update date and time" indicates the date and time when the workflow was recently updated. If the workflow has not been updated after it was newly registered, the "registration date and time" and the "update date and time" may be the same information, or information indicating that the update has not been made may be displayed as the "update date and time". Further, the "use model" indicates information that identifies the prediction models included in the workflow.

The example shown in FIG. 4A indicates that the "alias" corresponding to the "workflow ID" of "W0001" is "performance test 1", the "description" is "ooo", and the "registerer" is "U001", the "registration date and time" is "2018/08/01 10:00", and the "update date and time" is "2018/08/01 10:00", and indicates that it is the workflow that has not been updated after the registration. Further, it is indicated that the "use model" is "M0001, M0002 . . . ", and that a plurality of prediction models are used in the workflow.

FIG. 4B shows a data example of information regarding connection relationships among a plurality of prediction models included in the workflows stored in the workflow storage unit 324. As shown in FIG. 4B, the workflow storage unit 324 stores a "workflow ID", a "port ID", and a "connecting port" in association with one another.

Here, the "port ID" indicates a port ID of an input and output port included in a prediction model used in a workflow. Further, the "connecting port" indicates a port ID of a port connected with the port identified by the port ID indicated by the "port ID" of the "prediction model" in the workflow. If there is no port to be connected, it is indicated that there is no port to be connected, such as "None". Further, when the port is a part of the inputs or outputs of the entire workflow, the connection relationship is indicated by "input" or "output", respectively.

The example shown in FIG. 4B indicates that the "workflow ID" is "W0001", and the "connecting port" corresponding to the "port ID" of "M0001P01" is "M0002P02". It is indicated that among the prediction models used in the workflow identified by W0001, the port ID of the port connected to the port identified by "M0001P01" is "M0002P02". Further, as another example, it is indicated that the port identified by the "workflow ID" of "W0001" and the "port ID" of "M0001P02" is an "input", and one of the inputs of the entire workflow is inputted from that port.

The computation result storage unit 325 (an example of a result database) stores result of computations executed using the workflows and the execution parameters for executing the computations of the entire workflow.

Here, the results of the computations are obtained by sequentially executing a plurality of execution programs corresponding to the plurality of prediction models included in the workflow. Further, the computation result storage unit 325 stores not only the final computation result of the workflow obtained by sequentially executing the plurality of execution programs, but also information regarding the input and output data of each of the plurality of execution programs.

The computation result storage unit 325 stores information regarding the computation results and computation statuses, for example, as shown in FIG. 5A. Further, the computation result storage unit 325 stores information regarding the execution parameters, for example, as shown in FIG. 5B. Further, the computation result storage unit 325 stores information regarding computations of the execution programs corresponding to the respective prediction models included in the workflow, for example, as shown in FIG. 5C.

FIGS. 5A-SC are diagrams showing a data example of the computation result storage unit 325 according to the present embodiment.

FIG. 5A shows a data example of the information regarding the computation results stored in the computation result storage unit 325. As shown in FIG. 5A, the computation result storage unit 325 stores a "run ID", an "executor", an "description", a "workflow", a "status", an "execution parameter", an "execution date and time", a "completion date and time", a "computation job", and a "data storage" in association with one another.

Here, the "run ID" indicates identification information (an example of a unique identifier) for identifying an execution result. Further, the "executor" indicates information that identifies a user who executed the computation. Further, "description" indicates information that describes the computation to be executed. Further, the "workflow" indicates identification information such as a workflow ID of the workflow for which the computation is to be executed. Further, the "status" indicates information indicating the progress of the computation instructed to execute. The "status" indicates information indicating that the computation has not been executed, the computation is being executed, or the computation has been completed, as well as information indicating that the computation has been canceled by the user. Further, information such as an execution error may be indicated when the computation cannot be completed for some reason. Further, the "execution parameter" indicates information that identifies the information inputted to the input port of the workflow in order to execute the computation. Further, the "execution date and time" indicates the date and time when the computation of the entire workflow was started. Further, the "completion date and time" indicates the date and time when the computation of the entire workflow was completed. Further, the "computation job" indicates identification information that identifies computation processes for each execution program corresponding to the prediction model included in the workflow. Further, the "data storage" indicates information regarding a file that stores the computation result and a log at the time of the computation. Here, the log at the time of the computation is information including information such as the date and time when the computation was executed and the execution contents.

The example shown in FIG. 5A indicates that the "executor" corresponding to the "run ID" of "R0001" is "U001", the "description" is "W1_01", and the "status" is "completed". Further, it is indicated that the "execution parameter" is "R0001P001, R0001P002" which indicates that two types of execution parameters are given. Further, it is indicated that the "execution date and time" is "2018/08/01 10:00", and the "completion date and time" is "2018/08/01 10:02". Further, the "computation job" is "R0001J0001, R0001J0002", which indicates that two types of execution programs have been executed. Further, the "data storage" is "/ . . . /R0001/", which indicates that the computation result and the log at the time of computation are stored under the described directory.

FIG. 5B shows a data example of information regarding the execution parameters stored in the computation result storage unit 325. As shown in FIG. 5B, the computation result storage unit 325 stores an "execution parameter", a "name", a "type", "essential", a "unit", and a "parameter" in association with one another.

Here, the "name" indicates information of a descriptor that describes an execution parameter. For example, it may be an alias of the descriptor that describes the execution parameter. Further, the "type" indicates a format in which the execution parameter is given. Further, the "essential" indicates whether or not the execution parameter is an essential parameter for performing computations. Further, the "unit" indicates the unit of the execution parameter. Further, the "parameter" indicates a name of a file in which the execution parameter is saved. The file is saved under the above-described data storage directory.

The example shown in FIG. 5B indicates that the "name" corresponding to the "execution parameter" of "R0001P001" is "thermal history", the "type" is "File", the "essential" is "o", the "unit" is "[s, ° C.]" and the "parameter" is "input1.json", and indicates that this execution parameter is given by the file indicating the thermal history, and the data in the file includes a combination of time information and temperature information.

FIG. 5C shows a data example of information regarding computation jobs stored in the computation result storage unit 325. As shown in FIG. 5C, the computation result storage unit 325 stores a "computation job", a "job name", a "creation date and time", a "start date and time", and a "completion date and time" in association with one another.

Here, the "job name" indicates information indicating an execution program corresponding to a computation job. For example, the job name may be an alias of a prediction model that indicates the input and output relationship of the execution program. Further, the "creation date and time" indicates the date and time when the computation execution unit 334, which will be described later, reads the execution program when actually executing the computation using the execution program. Further, the "start date and time" indicates the date and time when the execution program started executing the computation. Further, the "completion date and time" indicates the date and time when the execution program completed the computation. Here, if the "creation date and time", the "start date and time", and the "completion date and time" do not exist for some reason (reading failed, computation could not be executed because input data could not be obtained, etc.), they may be left blank. Alternatively, a description indicating that the date and time data does not exist may be made. Here, data regarding the input and output of each execution program is a file with a name uniquely determined by using the identification information that identifies the computation job, and the file name is not described in FIG. 5C, but the example is not limited thereto.

The example shown in FIG. 5C indicates that the "job name" corresponding to the "computation job" of "R0001J0001" is "prediction model A", the "creation date and time" is "2018/08/01 10:00", the "start date and time" is "2018/08/01 10:00", and the "completion date and time" is "2018/08/01 10:02".

The relationship information storage unit 326 stores information regarding relationships among the above-mentioned descriptor, prediction model, workflow, and execution result (hereinafter, also referred to as "description format group"). The relationship information storage unit 326 describes and stores the relationships using RDF (Resource Description Framework), XML (Extensive Markup Language), or the like.

The relationship information storage unit 326 stores information regarding the relationship of the description format group, for example, as shown in FIG. 6.

FIG. 6 is a diagram showing a data example of the relationship information storage unit 326 according to the present embodiment.

In the example shown in FIG. 6, the relationship information storage unit 326 stores the relationship described in XML format. The XML that describes the relationship includes <run> to </run> that are tags indicating information of an execution result. The tags indicating the information of the execution result internally include a run ID that identifies the execution result, and <workflow> to </workflow> that are tags indicating information of a workflow targeted for execution of a computation. The tags indicating the information of the workflow internally include a workflow ID that identifies the workflow and <model> to </model> that are tags indicating information of a prediction model included in the workflow. The tags indicating the information of the prediction model internally include a prediction model ID that identifies the prediction model, and <port> to </port> that are tags indicating information of a port held by the prediction model. The tags indicating the information of the port internally includes a port ID that identifies the port, information indicating either an input or an output, information of a port to be connected, and <descriptor> to </descriptor> that are tags indicating information of a descriptor of data inputted and outputted via the port. The tags indicating the information of the descriptor internally include a descriptor ID that identifies the descriptor, and <file> to </file> that are tags indicating information regarding input and output data described in the descriptor. The tags indicating the information regarding the input and output data internally include information indicating a file name, and information indicating an address where the file is stored. Here, the expressions of the tags or the like which indicate the descriptor, the prediction model, the workflow, and the execution result are not limited to those described above. Further, each ID may be expressed by using the above-mentioned URI. In this case, the relationship may be RDF in XML format.

The user information storage unit 327 stores information regarding users who use the present system.

Figures 7, 8:
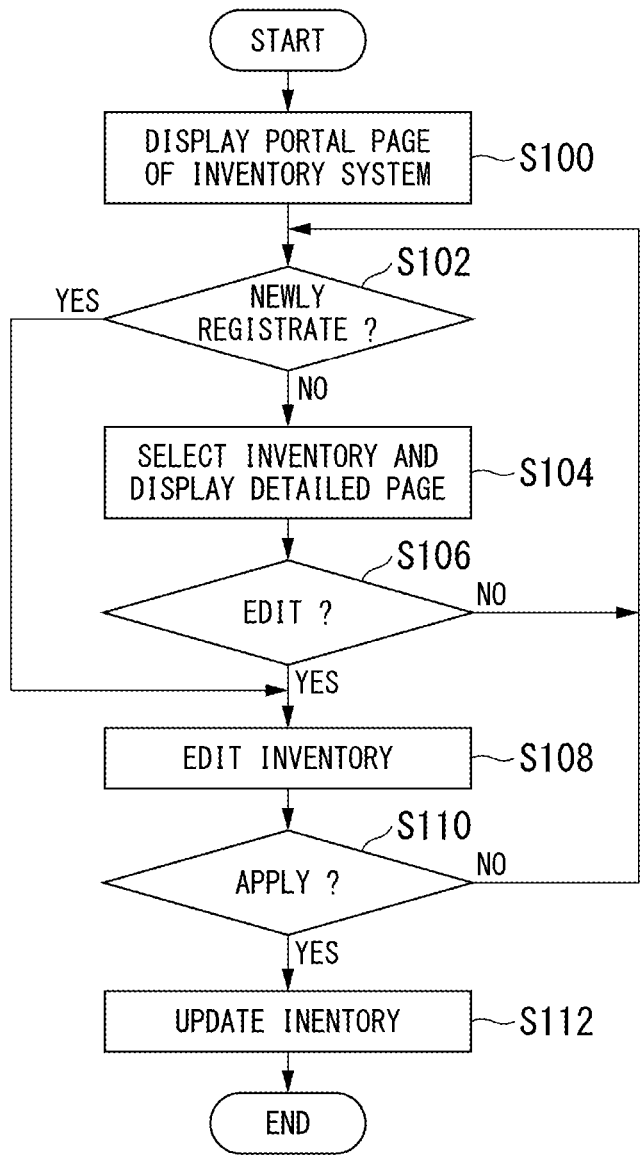
FIG. 7 is a diagram showing a data example of a user information storage unit according to the present embodiment.
FIG. 8 is a flowchart showing an example of processing regarding a descriptor according to the present embodiment.

FIG. 7 is a diagram showing a data example of the user information storage unit 327 according to the present embodiment.

As shown in FIG. 7, the user information storage unit 327 stores a "user ID", a "user name", and a "dictionary" in association with one another. Further, the "dictionary" indicates stored information of a descriptor and a prediction model (hereinafter, also referred to as "inventory") made available without search, for such a reason that users frequently use them. Further, the "dictionary" has a hierarchical structure, and the user can freely create a hierarchy and store the inventories in a hierarchy. There are a plurality of "dictionaries" each storing an "ID", a "dictionary position", and a "registration date and time" in association with one another. Here, the "ID" indicates identification information that identifies a registered inventory. Further, the "dictionary position" indicates information of the hierarchy in the "dictionary" registered by the user. Further, the "registration date and time" indicates the date and time when the user registered the inventory indicated by the ID.

The example shown in FIG. 7 indicates that the "user name" corresponding to the "user ID" of "U001" is "user A", the "affiliation group" is "0, 1", and the "ID" of "dictionary 1" is "D0001", the "dictionary position" is "/xxx/", and the "registration date and time" is "2018/06/10 10:30".

The processing unit 33 is a processor including, for example, a CPU and the like, and performs comprehensive control processing of the research and development support device 30. For example, the processing unit 33 receives from the user terminal 10, information indicating that a web application program is used, and transmits to the user terminal 10 based on the received information, information regarding the web application program. Further, the processing unit 33 receives from the user terminal 10, for example, information for executing a model construction, and based on the received information, transmits the information stored in the storage unit 32 to the user terminal 10 or updates the information stored in the storage unit 32. Further, the processing unit 33 receives from the user terminal 10, for example, information regarding an execution parameters for executing a computation, and executes the computation based on the received information. Further, the processing unit 33 receives from the user terminal 10, for example, information requesting a computation result, and transmits the computation result to the user terminal 10 based on the received information. Further, the processing unit 33 receives from the management terminal 20, for example, information requesting information of an updated prediction model, and transmits the information stored in the storage unit 32 based on the received information. Further, the processing unit 33 receives from the management terminal 20, for example, information regarding a setting of the updated prediction model, and updates the information stored in the storage unit 32 based on the received information. Further, the processing unit 33 receives from the user terminal 10, for example, information regarding a user of the system, and transmits the information stored in the storage unit 32 to the user terminal 10 based on the received information.

The processing unit 33 includes an acquisition unit 331, an API processing unit 332, a model processing unit 333, a computation execution unit 334, a user information processing unit 335, and an output unit 336.

The acquisition unit 331 acquires via the communication unit 31, various information inputted from the user terminal 10 and the management terminal 20 using the web browser. The acquisition unit 331 outputs the acquired information to the API processing unit 332.

The API processing unit 332 acquires the information outputted by the acquisition unit 331. The API processing unit 332 reads information regarding an API stored in the web application program storage unit 321, and based on the read information and the information acquired from the acquisition unit 331, analyzes the information from the user terminal 10 and the management terminal 20 (hereinafter, also referred to as "request information"). When the analyzed request information is information for displaying the web application, the API processing unit 332 reads information regarding the web application program from the web application program storage unit 321. The API processing unit 332 reads information regarding the API from the web application program storage unit 321 and converts, based on the read information, the information regarding the web application program into information expressed by using the API. The API processing unit 332 outputs the converted information to the output unit 336.

Further, when the request information is information regarding a description format group, the API processing unit 332 outputs the analyzed request information to the model processing unit 333. Further, when the analyzed request information is information regarding execution of a computation, the API processing unit 332 outputs the acquired information to the computation execution unit 334.

Further, the API processing unit 332 converts the response information acquired from the model processing unit 333 or the computation execution unit 334 into information expressed by using the API. The API processing unit 332 reads information regarding an API from the web application program storage unit 321 and converts the information acquired from the model processing unit 333 or the computation execution unit 334 into information expressed by using the API. The API processing unit 332 outputs the converted information to the output unit 336.

Further, when the request information is information regarding user information, the API processing unit 332 outputs the analyzed request information to the user information processing unit 335.

Further, the API processing unit 332 converts the response information acquired from the user information processing unit 335 into information expressed by using the API. The API processing unit 332 reads information regarding an API from the web application program storage unit 321 and converts the information acquired from the user information processing unit 335 into information expressed by using the API. The API processing unit 332 outputs the converted information to the output unit 336.

The model processing unit 333 performs processing regarding a description format group. The model processing unit 333 reads information from the storage unit that stores the description format group, based on the request information acquired from the API processing unit 332. Further, the model processing unit 333 causes the storage unit that stores the description format group to perform processing, based on the request information acquired from the API processing unit 332. Further, the model processing unit 333 outputs to the API processing unit 332, the read information and response information such as the result of processing performed by the storage unit.

The model processing unit 333 includes an inventory processing unit 3331 and a workflow processing unit 3332.

The inventory processing unit 3331 (an example of a registration processing unit) performs processing corresponding to the request information regarding the descriptor and the prediction model, which is acquired from the API processing unit 332. When the request information is information regarding new registration of a descriptor, the inventory processing unit 3331 causes the descriptor storage unit 322 to store the acquired information. Further, when the request information is information regarding update or deletion of a descriptor, the inventory processing unit 3331 causes the descriptor storage unit 322 to perform processing regarding the update or deletion of the descriptor. The inventory processing unit 3331 outputs to the API processing unit 332, as response information, information regarding whether or not the processing regarding the new registration or update of the descriptor has been completed. Further, when the request information is information regarding reading of a descriptor, the inventory processing unit 3331 reads the information regarding the descriptor from the descriptor storage unit 322 or the relationship information storage unit 326. The inventory processing unit 3331 outputs to the API processing unit 332, the read information as response information.

Further, when the request information is information regarding new registration of a prediction model, the inventory processing unit 3331 causes the prediction model storage unit 323 to store the acquired information. When the new registration has been completed based on the request information from the user of the user terminal 10, the inventory processing unit 3331 outputs to the API processing unit 332, as response information, information indicating that processing regarding registration by the user of the management terminal 20 has been completed. Further, when the request information is the information regarding the update or deletion of the prediction model, the inventory processing unit 3331 causes the prediction model storage unit 323 to perform the update or deletion processing on the prediction model. The inventory processing unit 3331 outputs to the API processing unit 332, as response information, information regarding whether or not the update or deletion based on the request information has been completed. Further, when the request information is the information regarding the reading of the prediction model, the inventory processing unit 3331 reads the information regarding the prediction model from the prediction model storage unit 323 or the relationship information storage unit 326. The inventory processing unit 3331 outputs to the API processing unit 332, the read information as response information.

Further, when the request information is information from the management terminal 20 regarding reading of information regarding a prediction model that needs to be processed by the administrator, the inventory processing unit 3331 reads from the prediction model storage unit 323, information of the prediction model that needs to be processed by the administrator, and outputs the read information to the API processing unit 332. Further, when the request information is information from the management terminal 20 regarding processing by the administrator for a prediction model, the inventory processing unit 3331 causes, based on the acquired information, the prediction model storage unit 323 to perform the processing on the prediction model. The inventory processing unit 3331 outputs to the API processing unit 332, as response information, information regarding whether or not the processing has been completed.

The details of the processing regarding the inventory processing unit 3331 will be described later.

The workflow processing unit 3332 performs processing corresponding to request information regarding a workflow, which is acquired from the API processing unit 332. When the request information is information regarding new registration of a workflow, the workflow processing unit 3332 causes the workflow storage unit 324 to store the acquired information. Further, when the request information is information regarding update or deletion of a workflow, the workflow processing unit 3332 causes the workflow storage unit 324 to perform processing regarding the update or deletion of the workflow. The workflow processing unit 3332 outputs to the API processing unit 332, as response information, information regarding whether or not the processing regarding the new registration, update, or deletion of the workflow has been completed.

Further, when the request information is information regarding reading of a workflow, the workflow processing unit 3332 reads the information regarding the workflow from the workflow storage unit 324. The workflow processing unit 3332 outputs to the API processing unit 332, the read information as response information.

The details of the processing regarding the workflow processing unit 3332 will be described later.

The computation execution unit 334 (an example of an execution unit) performs processing corresponding to request information regarding execution of a computation, which is acquired from the API processing unit 332. The computation execution unit 334 acquires information of an execution parameter included in the request information and causes the computation result storage unit 325 to store the acquired information. Further, the computation execution unit 334 acquires information of a workflow included in the request information, and reads the information of the workflow from the workflow storage unit 324. The computation execution unit 334 acquires information of a prediction model included in the read workflow, and acquires from the prediction model storage unit 323, an execution program corresponding to the prediction model. The computation execution unit 334 causes the computation result storage unit 325 to store the acquired information. The computation execution unit 334 executes a computation based on the acquired information and the information of the execution parameter. The computation execution unit 334 causes the computation result storage unit 325 to store information regarding a result of the execution of the computation. The computation execution unit 334 causes the computation result storage unit 325 to also store information on results of the inputting and outputting for each execution program corresponding to the prediction model. Further, when a computation result is obtained, the computation execution unit 334 causes the information storage unit 326 to store the computation result, and the information regarding the relationship among the workflow, the prediction model, the descriptor, and the input and output file, which are used for calculating the computation result. Further, the computation execution unit 334 outputs to the API processing unit 332, information regarding the computation result.

The details of the processing regarding the computation execution unit 334 will be described later.

The user information processing unit 335 performs processing corresponding to request information regarding user information, which is acquired from the API processing unit 332. The user information processing unit 335 acquires the user information included in the request information, and reads the user information from the user information storage unit 327. The user information processing unit 335 outputs the acquired information to the API processing unit 332.

Further, the computation result storage unit 325 acquires information for updating the information regarding the user, and causes the user information storage unit 327 to store the acquired information. The user information processing unit 335 outputs to the API processing unit 332, information regarding a result of the update processing regarding the user.

The output unit 336 performs a process of transmitting the response information to the user terminal 10 and the management terminal 20 via the communication unit 31, based on the information acquired from the API processing unit 332.

Next, operation of the prediction management system 1 according to the present embodiment will be described with reference to the drawings.

[Processing of Inventory System Regarding Descriptors]

First, an example of processing regarding descriptors performed by the inventory system in a data storage method according to the present embodiment will be described with reference to FIG. 8. FIG. 8 is a flowchart showing an example of the processing regarding descriptors according to the present embodiment.

First, the user of the user terminal 10 (hereinafter, also referred to as "system user"), by using the web browser, logs in to the inventory system, the workflow design system, and the workflow execution system at a gateway (not shown) on the network NW. After logging in, the system user chooses to use the inventory system.

The research and development support device 30 acquires from the user terminal 10, request information regarding a portal page of the system user in the inventory system. Here, the portal page of the system user is a page or the like displayed for the request information of a URI indicated by using the user ID of the system user. Here when the user ID is a URI, the page may be displayed in response to the request information of that URI. The acquisition unit 331 outputs the acquired information to the API processing unit 332. After analyzing the acquired information, the API processing unit 332 acquires from the user information storage unit 327, information regarding the user ID, based on the user ID included in the request information. The API processing unit 332 generates response information based on the acquired information and transmits the generated response information to the user terminal 10. Here, the response information is information that displays the portal page. The user terminal 10 causes the display unit 13 to display the portal page based on the received response information (step S100).

Figure 9:
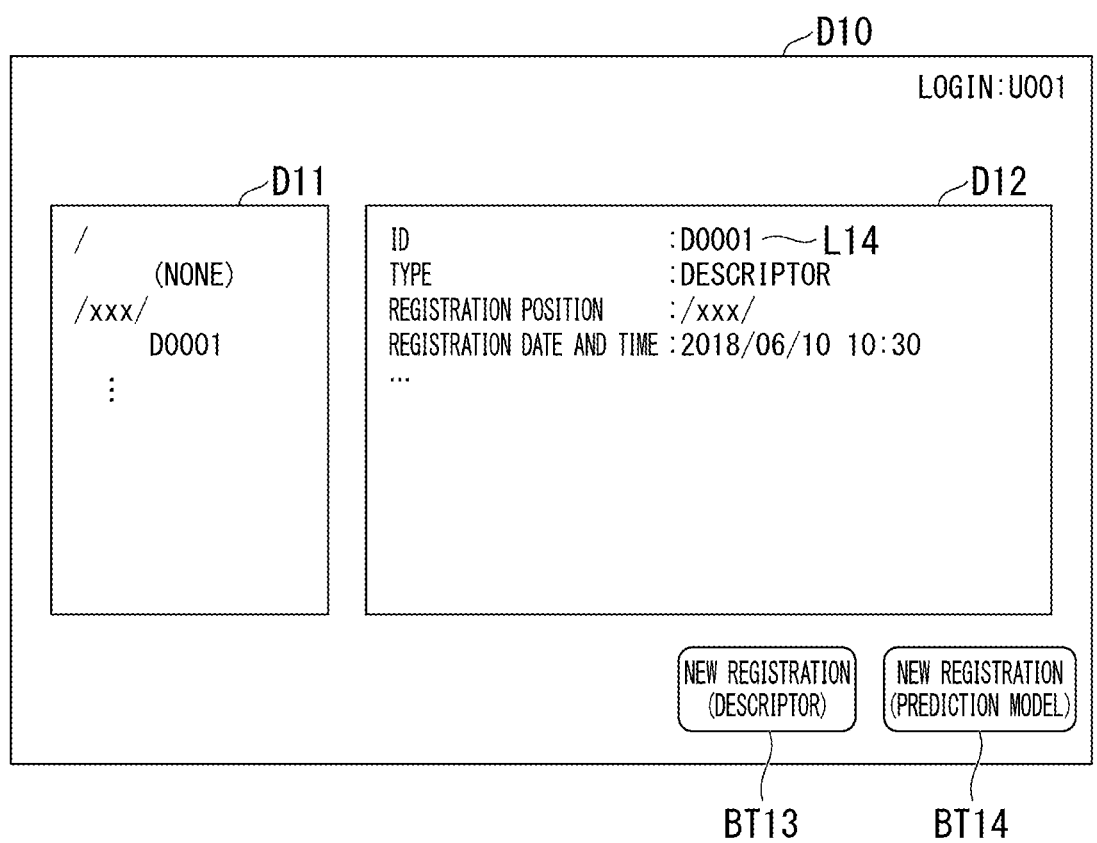
FIG. 9 is a diagram showing an example of a portal page of an inventory system that performs processing regarding a descriptor and a prediction model according to the present embodiment.

FIG. 9 is a diagram showing an example of a portal page of the inventory system according to the present embodiment.

The user terminal 10 displays a display screen D10 of the portal page on the web browser when the inventory system is selected by the system user. The display screen D10 includes a dictionary display unit D11, a selected inventory display unit D12, a new descriptor creation button BT13, and a new prediction model creation button BT14. Here, the dictionary display unit D11 is an area for displaying a dictionary of the system user. Further, the selected inventory display unit D12 is an area for displaying information regarding an inventory when the inventory is selected from the dictionary display unit D11. Further, the new descriptor creation button BT13 is a button for creating a new descriptor. Further, the new prediction model creation button BT14 is a button for creating a new prediction model. When the user terminal 10 displays the display screen D10, the process proceeds to step S102.

When the new descriptor creation button BT13 is pressed (step S102: YES), the user terminal 10 transmits request information regarding the creation of a new descriptor to the research and development support device 30. Then, the process proceeds to step S108. A case where the new prediction model creation button BT14 is pressed will be described later. When the new creation buttons BT13 and BT14 are not pressed (step S102: NO), the user terminal 10 proceeds to the process in step S104.

When the input unit 12 of the user terminal 10 receives an input to select an inventory displayed on the dictionary display unit D11, the user terminal 10 transmits to the research and development support device 30, request information requesting information regarding the inventory. Based on the received request information, the research and development support device 30 acquires the information regarding the inventory from the descriptor storage unit 322 or the prediction model storage unit 323, and generates response information for displaying the selected inventory display unit D12. The research and development support device 30 transmits the generated response information to the user terminal 10. The user terminal 10 displays the received response information on the selected inventory display unit D12.

FIG. 9 shows a state in which information regarding the descriptor D0001 is displayed on the selected inventory display unit D12 when the user selects the descriptor D0001 in the dictionary display unit D11. Here, the selected inventory display unit D12 displays information regarding the user dictionary in which the inventory is registered. For example, an inventory ID (descriptor ID or prediction model ID) that identifies the inventory, a type of the inventory, a registered position in the user dictionary of the inventory (information such as a directory), and the date and time of the registration in the user dictionary, and the like are displayed in the selected inventory display unit D12 of FIG. 9.

Further, the inventory ID includes a link L14 to a page that displays the details of the inventory. Here, the link L14 is not always included in the inventory ID. For example, it may be represented by another element, such as a button separately displayed in the selected inventory display unit D12.

When the link from the link L14 is selected by the system user, or when the system user makes an input to display detailed information of the inventory searched by the inventory search or the like, the user terminal 10 transmits to the research and development support device 30, request information requesting information regarding the detailed information of the inventory. The research and development support device 30 acquires information regarding the inventory from the descriptor storage unit 322 or the prediction model storage unit 323, based on the received information. Further, based on the received information, the research and development support device 30 acquires from the user information storage unit 327, information regarding the dictionary in which the descriptor is registered. The research and development support device 30 transmits to the user terminal 10, response information including the acquired information. Here, the response information is a web page (hereinafter, also simply referred to as "page") that displays the detailed information of the inventory. The user terminal 10 displays the received information.

FIGS. 10A and 10B are diagrams showing examples of web pages regarding the detailed information of the descriptor according to the present embodiment.

FIG. 10A shows an example of a web page displayed when browsing the detailed information of the descriptor according to the present embodiment. When the system user makes a selection to display the detailed information of the descriptor, the user terminal 10 displays on the web browser, a descriptor detail screen D20 that displays the detailed information of the descriptor, based on the information received from the research and development support device 30 (step S104). The descriptor detail screen D20 includes, for example, detailed information regarding the descriptor, information indicating a structure of data accepted by the descriptor, information regarding the prediction model in which the descriptor is used, a button BT23 for editing the information regarding the descriptor, and the like.

In FIG. 10A, the descriptor detail screen D20 displays, as detailed information regarding the descriptor identified by "D0001", detailed information such as a descriptor ID, an alias, a registerer, a dimension, a unit, a description, a registration date and time, an update date and time, and the like. Further, the descriptor detail screen D20 displays a file name indicating the structure of the data accepted by the descriptor, and a link L21 to that file. Here, a link to the JSON file shown in FIG. 2B is shown. Further, the descriptor detail screen D20 displays in an import dictionary field, information regarding the dictionary in which the descriptor is imported. Here, the dictionary to be displayed may be set to be public or private to other users for each directory of the dictionary. In this case, information regarding other users is displayed in the import dictionary field when the descriptor is set to be public and registered.

Further, in FIG. 10A, the descriptor detail screen D20 displays in a model field, information that identifies the prediction model in which the descriptor is used, and a link L22 to a page that displays the detailed information of the prediction model. Here, the information that identifies the prediction model displays the name registered as the alias of the prediction model, but is not limited thereto. For example, the ID of the prediction model may be displayed. Further, in the example shown in FIG. 10A, the display is made without distinguishing whether the descriptor is an input descriptor connected to the input port of the prediction model or an output descriptor connected to the output port, but the display may be made by distinguishing these.

In FIG. 10A, when the button BT23 is pressed by the system user (step S106: YES), the user terminal 10 transmits to the research and development support device 30, information regarding editing of the descriptor, as request information. The research and development support device 30 performs a process of starting editing based on the received information. Here, the process of starting the editing is a process of preventing another user from editing the descriptor, or the like. The research and development support device 30 transmits to the user terminal 10, information including a page for editing the descriptor, as response information.

The user terminal 10 displays an edit screen on the web browser based on the received information, and proceeds to step S108. When the system user does not make the input to press the button BT23 (step S106: NO), the system user returns to step S102, and selects and browses another inventory, or performs a process of creating a new inventory.

FIG. 10B shows an example of a web page displayed when editing the detailed information of the descriptor. When a selection to edit on the descriptor detail screen is made, or when a selection to newly register a descriptor on the portal page is made, the user terminal 10 displays on the web browser, a descriptor edit screen D24 as shown in FIG. 10B, based on the information received from the research and development support device 30. When creating a new descriptor, the research and development support device 30 refers to the storage unit 32, sets an ID that has not been used so far, as a new descriptor ID, and transmits to the user terminal 10, information regarding the descriptor edit screen D24 for editing that descriptor ID.

The descriptor edit screen D24 includes, for example, an edit unit TB25 for editing detailed information of a descriptor, an update button BT26 for updating the edited information, a cancel button BT27 for discarding the edited information, and the like. In FIG. 10B, the descriptor edit screen D24 shows a screen for editing detailed information regarding the descriptor identified by "D0001". In the edit unit TB25, the system user enters the edited information, or selects a file in which the structure is shown (step S108). The update button BT26 is a button for instructing the update of the information of the descriptor by using the edited information. The cancel button BT27 is a button for discarding the edited information and instructing to cancel editing the descriptor. After receiving from the system user, the input for editing the information regarding the descriptor, the user terminal 10 proceeds to the process in step S110.

When the update button BT26 is pressed by the system user (step S110: YES), the user terminal 10 transmits information regarding the update of the descriptor to the research and development support device 30. The research and development support device 30 proceeds to the process in step S112.

Further, when the cancel button BT27 is pressed by the system user (step S110: NO), the user terminal 10 transmits to the research and development support device 30, information to cancel updating the descriptor. Based on the received information, the research and development support device 30 cancels the process regarding the update, and returns to step S102. Here, the process regarding the update is a process of canceling the setting that prevents other users from editing the descriptor. Further, when the information for canceling the new registration of a descriptor is received, as a process regarding the update, a process of changing an assigned new ID to a state in which it can be used for another descriptor, or the like, is performed.

The research and development support device 30 receives from the user terminal 10, the information regarding the update of the descriptor, and updates the information of the descriptor in the descriptor storage unit 322, based on the received information (step S114). In the case of new creation, the research and development support device 30 newly adds information of a descriptor to the descriptor storage unit 322. Further, the research and development support device 30 performs a process of changing or adding the setting information regarding the descriptor in the web application program storage unit 321, and ends the process of updating the descriptor.

[Processing of Inventory System Regarding Prediction Model]

Figure 11:
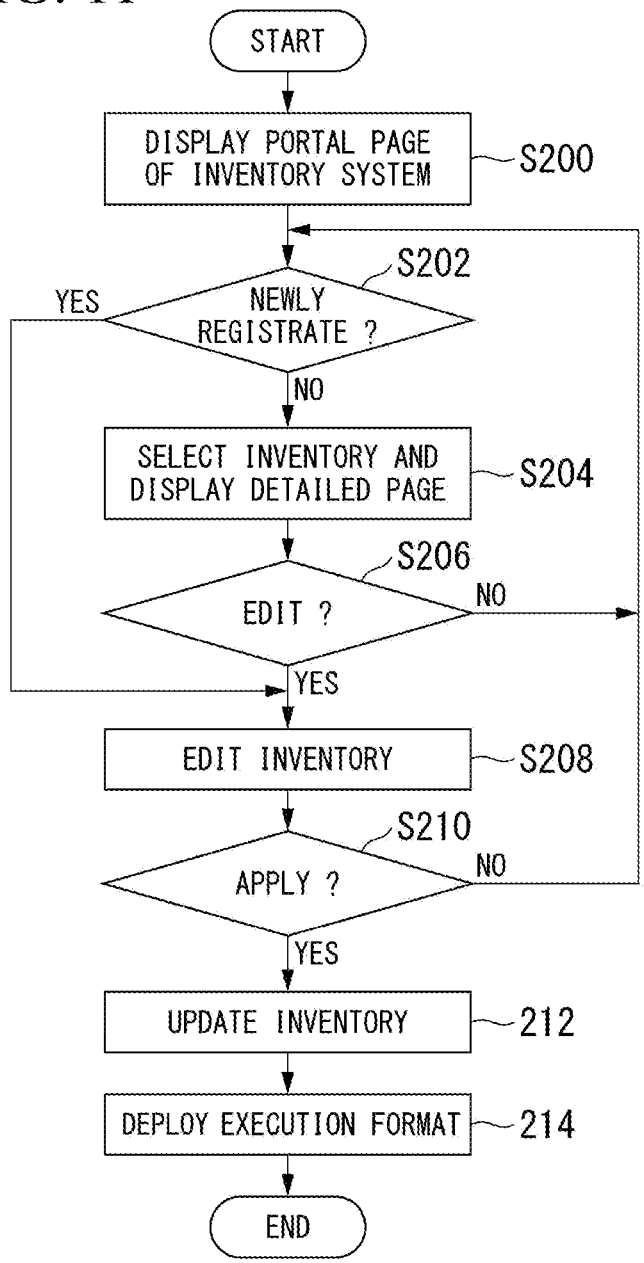
FIG. 11 is a flowchart showing an example of processing regarding the prediction model according to the present embodiment.

Subsequently, an example of processing regarding the prediction model performed by the inventory system in the data storage method according to the present embodiment will be described with reference to FIG. 11. FIG. 11 is a flowchart showing an example of the processing regarding the prediction model according to the present embodiment.

In FIG. 11, step S200 is the same as step S100, and thus a description thereof will be omitted. After step S200, the user terminal 10 proceeds to the process in step S202.

In FIG. 9, when the new prediction model creation button BT14 is pressed (step S202: YES), the user terminal 10 transmits to the research and development support device 30, request information regarding new creation of a prediction model. Then, the process proceeds to step S208. When the new creation buttons BT13 and BT14 are not pressed (step S202: NO), the user terminal 10 proceeds to the process in step S204. Here, the display in FIG. 9 of the dictionary display unit D11 and the selected inventory display unit D12 is the same as in the case of the descriptor, and thus a description thereof will be omitted.

Figure 12A:
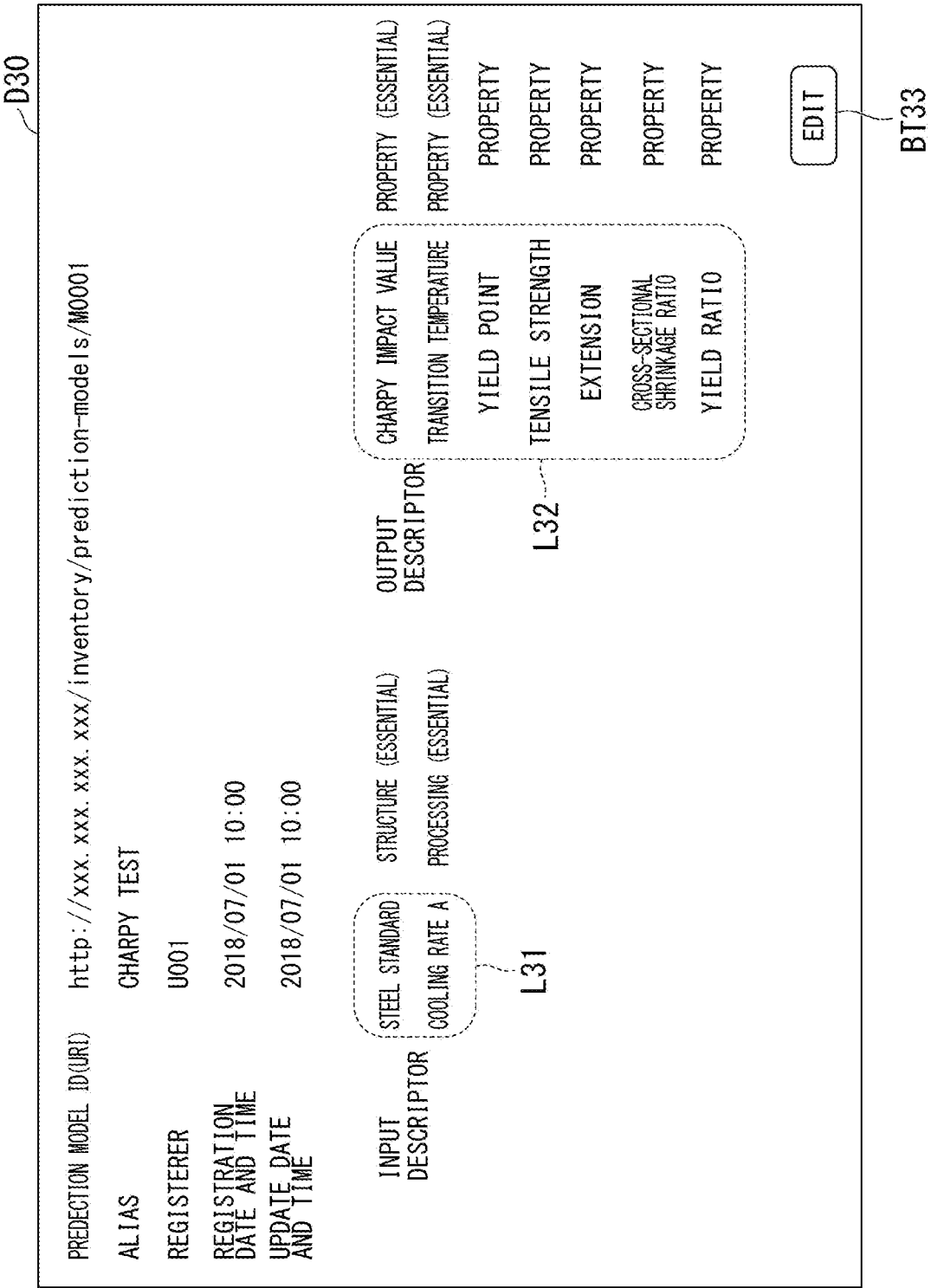
FIG. 12A is a diagram showing an example of a web page displayed when browsing detailed information of a prediction model according to the present embodiment.

FIGS. 12A and 12B are diagrams showing examples of web pages regarding detailed information of the prediction model according to the present embodiment.

FIG. 12A shows an example of a web page displayed when browsing the detailed information of the prediction model. When the system user makes a selection to display the detailed information of the prediction model, the user terminal 10 displays on the web browser, a prediction model detail screen D30 for displaying the detailed information of the prediction model, based on the information received from the research and development support device 30 (step S204). The prediction model detail screen D30 includes, for example, detailed information regarding the prediction model, information regarding input descriptors and output descriptors connected to the prediction model, information regarding the input and output ports to and from which the descriptors are inputted and outputted, a button BT33 for editing the information of the prediction model, and the like.

In FIG. 12A, the prediction model detail screen D30 displays, as the detailed information regarding the prediction model identified by "M0001", detailed information such as an ID, an alias, a registerer, a registration date and time, and an update date and time of the prediction model. Further, the prediction model detail screen D30 displays information regarding the input descriptors and the output descriptors to which the prediction model is connected, and links L31 and L32 to the respective descriptors. Here, the aliases of the descriptors are displayed as information indicating the input descriptors and the output descriptors, but the example is not limited thereto. For example, information such as the ID and type of a descriptor may be displayed. Further, the prediction model detail screen D30 displays information regarding the ports to and from which the descriptors are inputted and outputted. In FIG. 12A, it is shown that the input port to which the input descriptor "steel standard" is inputted is classified into the structure, and the input from that input port is essential.

In FIG. 12A, when the button BT33 is pressed by the system user (step S206: YES), the user terminal 10 transmits to the research and development support device 30, information regarding editing of the prediction model, as request information. The research and development support device 30 performs a process of starting editing based on the received information. Here, the process of starting the editing is a process of preventing other users from editing the prediction model, or the like. The research and development support device 30 transmits to the user terminal 10, information including a page for editing the prediction model, as response information. The user terminal 10 displays an edit screen on the web browser based on the received information, and proceeds to step S208. If the button BT33 is not pressed (step S206: NO), the system user returns to step S202, selects and browses another inventory, or newly creates an inventory.

FIG. 12B shows an example of a web page displayed when editing the detailed information of the prediction model. When the system user makes a selection to perform editing on the detailed screen of the prediction model, or when the system user makes a selection to newly register a prediction model on the portal page, the user terminal 10 displays on the web browser, a prediction model edit screen D34, as shown in FIG. 12B, based on the information received from the research and development support device 30. When a prediction model is newly created, the research and development support device 30 refers to the storage unit 32, sets an ID that has not so far been used as a new prediction model ID, and transmits to the user terminal 10, information regarding the prediction model edit screen D34 for editing the prediction model ID.

The prediction model edit screen D34 includes, for example, an alias of the prediction model, an edit unit TB35 for editing an execution program corresponding to the prediction model, a selection unit TB36 of input descriptors to which the prediction model is connected, a selection unit TB37 of output descriptors, an application button BT38 for applying for update of edited information, a cancel button BT39 for discarding the edited information, and the like. In FIG. 12B, the prediction model edit screen D34 shows a screen for editing detailed information regarding the descriptor identified by "M0001". In the edit unit TB35, the system user enters the edited information or selects a file indicating an execution program. The descriptor selection units TB36 and TB37 include two components which are: a descriptor input unit for selecting from the descriptors registered in the inventory system, a descriptor to which the prediction model is connected; and a port selection unit for selecting a type of input and output from the port to or from which the descriptor is inputted or outputted, together with whether or not the input and output to and from the port is essential. The type of input and output is selected from one of the predefined "processing means", "structure", "property", and "performance". In the descriptor selection units TB36 and TB37, a descriptor and port information are selected by the system user. Here, when updating the prediction model, a restriction may be imposed to prohibit the editing of the input and output port and the execution program so as to prevent the execution program corresponding to the prediction model from being erroneously executed before and after the update. In this case, a configuration may be such that only the descriptor that matches the corresponding port type is selectable.

The application button BT38 is a button for instructing to apply for update of the information of the prediction model using the edited information. The cancel button BT39 is a button for discarding the edited information and instructing to cancel editing of the prediction model. The user terminal 10 receives an input for editing the information regarding the prediction model from the system user by the method described above (step S208), and then proceeds to the process in step S210.

When the application button BT38 is pressed by the system user (step S210: YES), the user terminal 10 transmits to the research and development support device 30, information regarding the update of the prediction model. The research and development support device 30 proceeds to the process in step S212.

Further, when the cancel button BT39 is pressed by the system user (step S210: NO), the user terminal 10 transmits to the research and development support device 30, information to cancel updating the prediction model. Based on the received information, the research and development support device 30 cancels the process regarding the update and returns to step S202. Here, the process regarding the update is a process of canceling the setting that prevents other users from editing the prediction model, or the like. Further, when information for canceling the new registration of the prediction model is received, as the process regarding the update, a process of changing the assigned new ID to a state where it can be used for another prediction model again, or the like, is performed.

When the information regarding the application for updating the prediction model is received from the user terminal 10, the research and development support device 30 causes the prediction model storage unit 323 to store the received information and information indicating that the information has not been processed by the management terminal 20. Here, the research and development support device 30 may transmit to the management terminal 20, information indicating that the application for updating the prediction model has been made.

The management terminal 20 receives from the research and development support device 30, the information regarding the application for updating the prediction model, based on the information inputted by a user of the management terminal 20 (hereinafter, also referred to as "administrator"). The management terminal 20 accepts the input from the administrator and transmits to the research and development support device 30, information for performing a process of changing or adding the setting information of the information regarding the prediction model in the web application program storage unit 321, based on the information regarding the prediction model for which the update application has been made. The research and development support device 30 updates the information in the web application program storage unit 321 according to the received information (step S212). Subsequently, the management terminal 20 and the research and development support device 30 proceed to the process in step S214.

The management terminal 20 accepts an input from the administrator and transmits to the research and development support device 30, information for storing the execution program corresponding to the prediction model in a predetermined storage location of the prediction model storage unit 323. Based on the received information, the research and development support device 30 performs a process of storing the execution program in the predetermined storage location of the prediction model storage unit 323.

Further, the management terminal 20 transmits to the research and development support device 30, information for changing the information not registered by the administrator to registered information, among the information regarding the prediction model in the prediction model storage unit 323. The research and development support device 30 changes the information in the prediction model storage unit 323 based on the received information (step S214), and ends the process regarding the prediction model.

[Processing of Workflow Design System]

Figure 13:
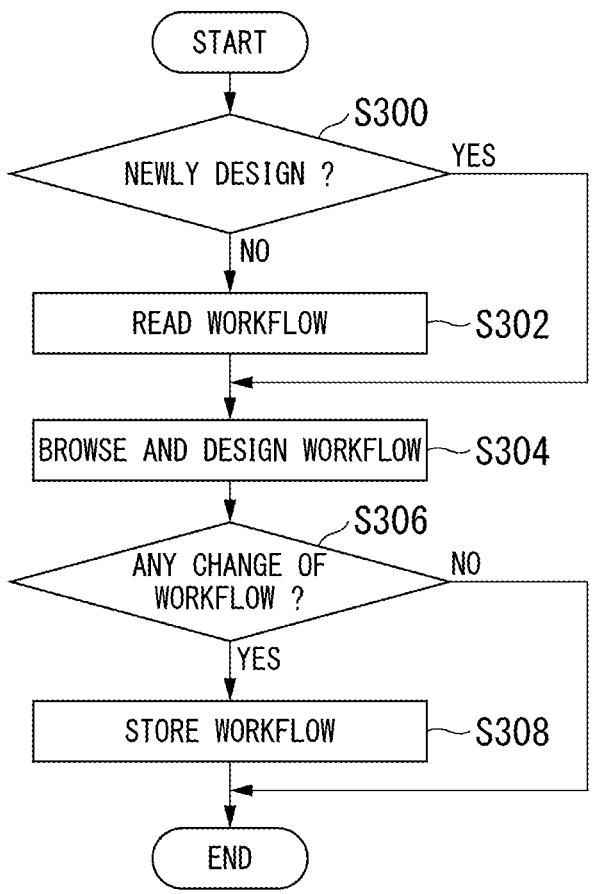
FIG. 13 is a flowchart showing an example of workflow processing according to the present embodiment.

Next, an example of workflow processing in the data storage method according to the present embodiment will be described with reference to FIG. 13. FIG. 13 is a flowchart showing an example of the workflow processing according to the present embodiment.

First, after the above-described login process from the gateway, the user terminal 10 accepts an input by the system user for selecting the workflow design system and transmits the accepted information to the research and development support device 30. Based on the received information, the research and development support device 30 reads a program that executes the workflow design system and transmits the read program to the user terminal 10. Further, the research and development support device 30 transmits to the user terminal 10 based on the received information, information for selecting whether to newly design a workflow or change the design of the existing workflow (step S300).

When the system user makes an input indicating that a workflow is to be newly designed (step S300: YES), the user terminal 10 transmits the information to the research and development support device 30. The research and development support device 30 receives the information and proceeds to the process in step S304.

When the system user makes an input indicating that the design of the existing workflow is to be changed (step S300: NO), the user terminal 10 transmits the information to the research and development support device 30. The research and development support device 30 receives the information and proceeds to the process in step S302.

When the information for changing the design of the existing workflow is received, the research and development support device 30 transmits to the user terminal 10, information including a page for selecting a workflow subject to the design change. The user terminal 10 displays the received page on the web browser. Subsequently, an input of information specifying the workflow is received from the system user, and the information is transmitted to the research and development support device 30. The research and development support device 30 reads the received workflow information from the workflow storage unit 324. Further, the research and development support device 30 reads from the web application program storage unit 321, an application program for executing the workflow. The research and development support device 30 transmits the read information to the user terminal 10. The user terminal 10 executes the program of the received workflow design system and displays the received workflow information on the program (step S302).

Figure 14A:
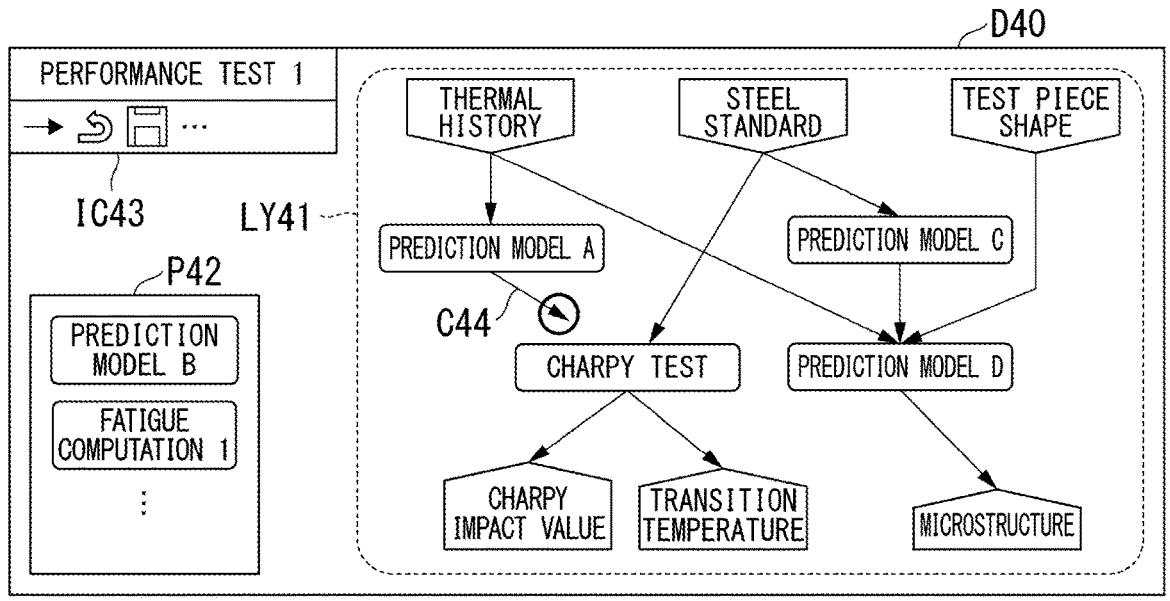
FIG. 14A is a diagram showing an example of a design screen in a workflow design system according to the present embodiment.
Figure 14B:
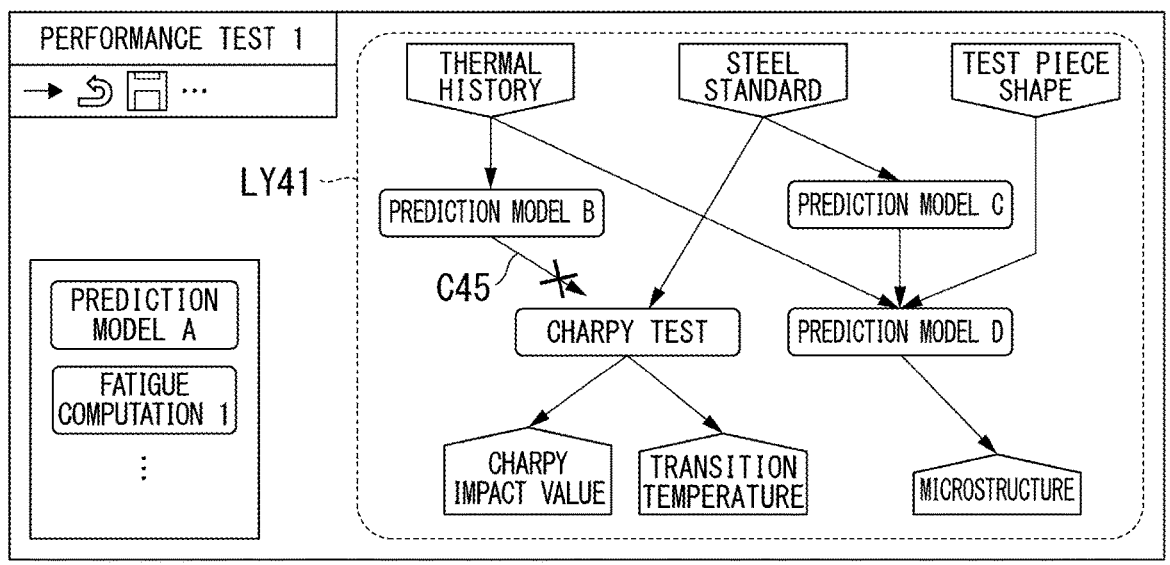
FIG. 14B is a diagram showing another example of a design screen in the workflow design system according to the present embodiment.
Figure 14C:
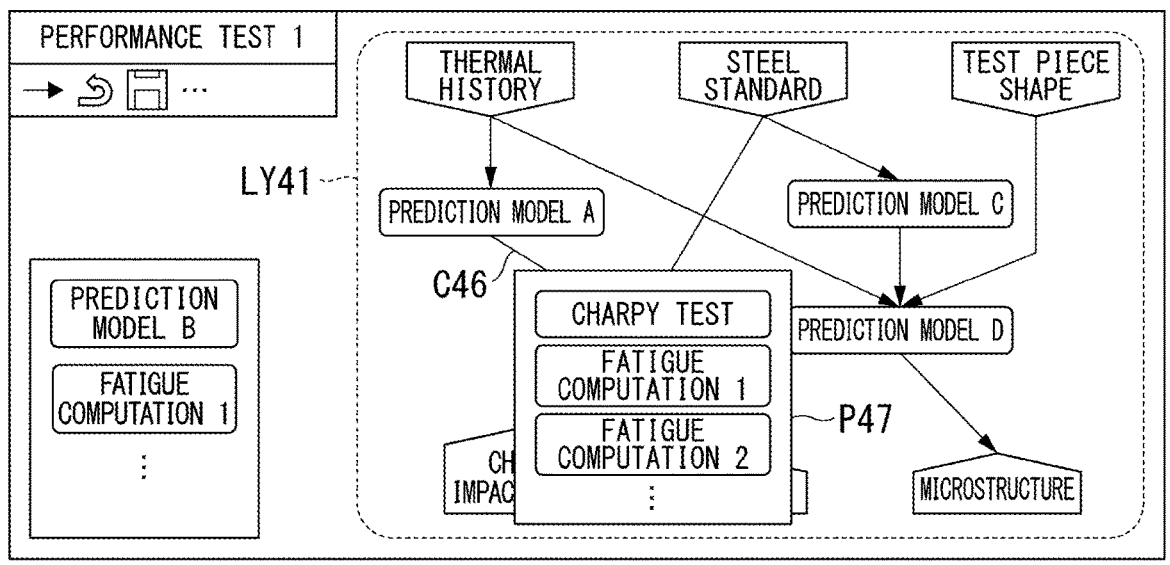
FIG. 14C is a diagram showing another example of a design screen in the workflow design system according to the present embodiment.

FIGS. 14A to 14C are diagrams showing examples of a design screen in the workflow design system according to the present embodiment.

As shown in FIG. 14A, the user terminal 10 reads the received workflow information on the web application program and displays a workflow design screen D40 on the web browser. The workflow design screen D40 includes, for example, a workflow display unit LY41, a prediction model palette display unit P42, and an operation icon display unit IC43. The workflow display unit LY41 is a display unit that graphically displays the read workflow. The prediction model palette display unit P42 is a display unit that graphically displays a list of prediction models already registered by the administrator, which are the prediction models loaded into the web application program and available for designing a workflow. The operation icon display unit IC43 is a display unit that displays an icon for selecting an operation when designing a workflow.

The workflow display unit LY41 graphically displays connection relationships among a plurality of prediction models included in the workflow.

In the example shown in FIG. 14A, the rounded quadrangular figures displayed as "prediction model A", "prediction model B", "prediction model C", "prediction model D", "Charpy test", and "fatigue computation 1", indicate the respective prediction models. Each figure displays information that identifies the corresponding prediction model. In FIG. 14A, for example, an alias of the prediction model is displayed on the figure.

Further, the pentagonal figures displayed as "steel standard", "thermal history" and "test piece shape" indicate input ports that accept inputs of data in the format described in the descriptors when executing the computations using the workflow. Further, the pentagonal figures displayed as "Charpy impact value", "transition temperature" and "microstructure" indicate output ports from which data in the format described in the descriptors are outputted when the computations are executed using the workflow. Information that identifies the descriptor associated with each input port is displayed on each input and output port. In FIG. 14A, for example, the aliases of the descriptors are displayed on the figures. The shapes of these figures are not limited to the above-described shapes.

The arrows connecting the input port, the output port, and the prediction model indicate information regarding the connections among the input port, output port, and prediction model. Here, the information regarding the connections is information indicating the order in which the input and output ports and the prediction model are connected, and indicates the input and output direction of data used for computations when the computations are executed using the workflow.

For example, the "prediction model A" accepts as an input, heat history which is one of the processing means, and outputs a cooling rate which is one of the processing means. The "prediction model C" accepts as an input, a steel standard which is one of the structures, and outputs a chemical composition which is one of the processing means. The "prediction model D" accepts as inputs, the thermal history, the chemical composition, and a test piece shape which is one of the structures, and outputs a microstructure which is one of the structures.

Further, the "Charpy test" accepts as inputs, the steel standard, the cooling rate, and the chemical composition, and outputs a Charpy impact value and a transition temperature which are the descriptors of the property. Here, in FIG. 14A, the output is one type of processing means, structure, property, and performance, but the output is not limited thereto. A plurality of types out of the above-described four types may be outputted. When there are a plurality of types of outputs, a combination thereof may be any combination of the four types described above, and the number of outputs of each type is not limited to one. Further, the type of input is not limited to the above-described combination. The descriptor to be the input may be any combination of the four types, and the number of inputs of each type is not limited to one.

The descriptors are not explicitly displayed on the workflow display unit LY41. If two prediction models are connected via an arrow, it is indicated that the prediction models are connected via a descriptor. For example, the chemical composition, which is the output descriptor of the prediction model C, is not displayed in FIG. 14A, but the prediction model C and the prediction model D are connected via the chemical composition. Further, if multiple descriptors are present in a prediction model, the arrow indicates that the prediction models are connected via at least one of the descriptors. Further, when the input and output port and the prediction model are connected by an arrow, it is indicated that data described by the descriptor of the prediction model is the input and output data when calculating the entire workflow. Here, the expression of the arrow may be changed according to the number of connected descriptors. For example, the number of connected descriptors may be displayed adjacent to the arrow. Further, the expression of the arrow may be changed between the case where all descriptors are connected and the other case.

The workflow display unit LY41 in FIG. 14A shows a state in which a workflow for performing a computation for obtaining two output data using two input data is being designed. The prediction model and the input and output port can be connected by, for example, selecting a figure of the arrow from the operation icon display unit IC43 and performing an operation such as dragging between the figures to be connected.

When the user terminal 10 displays the workflow design screen D40, the process proceeds to step S304.

The example shown in FIG. 14A shows a state of the workflow design screen D40 when the system user connects the prediction model A and the Charpy test. When the system user performs an operation of connecting the output from the prediction model A and the input to the Charpy test, the user terminal 10 displays an arrow on the workflow display unit LY41 in accordance with the drag. Further, the user terminal 10 performs a determination process of determining whether or not the prediction model A and the Charpy test can be connected.

For example, when the same descriptor exists between the output descriptor and the input descriptor, the determination process determines that the prediction models can be connected via the descriptor. Here, the same descriptor means the descriptors having the same descriptor ID. Further, when the output descriptor and the input descriptor are descriptors of the same type, it is determined that the prediction models can be connected via the descriptor. Here, the descriptors of the same type are, for example, descriptors for which the input and output ports to and from which the descriptors are inputted and outputted are of the same classification. Alternatively, the descriptors of the same type are a case such that in the information items indicating the structures of the output descriptor and the input descriptor, the information items can be treated as the same information by performing some conversion process, such as when the units are different, but the same physical quantity is expressed by converting the units.

If the connection is possible as a result of the determination process, the arrow may be displayed including information indicating that the connection is possible. In FIG. 14A, the user terminal 10 displays an arrow C44 added with a circle indicating that the connection is possible as a result of the determination process. When the drag is completed and the two figures are connected via the arrow, the arrow C44 is changed to, and displayed as, an arrow without the circle indicating that the connection is possible.

The example shown in FIG. 14B shows a state after the prediction model A has been changed to the prediction model B. Here, when a prediction model is newly used in the workflow, the system user can use the prediction model in the workflow by, for example, dragging to the workflow display unit LY41, a figure indicating the prediction model displayed on the prediction model palette display unit P42.

Here, when the system user performs an operation of connecting the output from the prediction model B and the input to the Charpy test, the user terminal 10 performs the above-described determination process. As a result of the determination process, if the connection is not possible, the user terminal 10 displays an arrow C45 added with a mark indicating that the connection is not possible. The arrow displayed with the arrow C45 cannot connect the prediction models even by the dragging. Here, if the connection is not possible, the user terminal 10 may perform a process of not displaying the arrow. Alternatively, an arrow different from the arrow indicating the connectable state may be displayed, such as changing the color of the arrow.

The example shown in FIG. 14C shows a state in which the system user is dragging an arrow C46 from the prediction model A to an area of the workflow display unit LY41 where there is no figure to be connected. Here, the area where there is no figure to be connected means an area where there is no connectable figure (prediction model, input and output port), regardless of whether the connection is possible or impossible to the area adjacent to the tip of the arrow C46. In this case, the user terminal 10 may display in the area where there is no connectable figure, a connectable pallet display unit P47 that displays a list of connectable prediction models. At this time, the user terminal 10 transmits to the research and development support device 30, information requesting information regarding a prediction model that can accept the output descriptor of the derivation module as an input descriptor. The research and development support device 30 acquires, based on the received information, information regarding the corresponding prediction model from the prediction model storage unit 323, the relationship information storage unit 326, or the like, and transmits the acquired information to the user terminal 10. The user terminal 10 displays the connectable pallet display unit P47 based on the received information. When the user terminal 10 accepts an input by the system user for selecting a prediction model from the connectable pallet display unit P47, the user terminal 10 cancels displaying the connectable pallet display unit P47, connects the selected prediction model with an arrow, and displays the selected prediction model on the workflow display unit LY41.

The system user designs a workflow by repeating the above work. When the user terminal 10 accepts an input for saving the workflow by the system user selecting an icon for saving the workflow on the operation icon display unit IC43 or giving an instruction to save the workflow by another input method, the user terminal 10 proceeds to the process in step S306. Further, also when the user terminal 10 accepts an input for discarding the change in the connection state of the workflow, the user terminal 10 proceeds to the process in step S306.

When the system user changes the workflow connection state shown in the workflow display unit LY41 (step S306: YES), the user terminal 10 proceeds to the process in step S308. Here, the case where the connection state is changed is a case where the connection between a prediction model and an input and output port is changed by changing the figure, changing the connection of the arrow, or the like. When the connection state of the workflow display unit LY41 is not finally changed, or when the user terminal 10 accepts an input for discarding the change of the connection state (step S306: NO), the user terminal 10 performs a process of canceling the display of the workflow in the workflow display unit LY41 and ends the processing.

The user terminal 10 transmits the changed workflow information to the research and development support device 30. The research and development support device 30 performs a process of updating the information stored in the workflow storage unit 324, based on the received information (step S308). Thereafter, the processing ends.

[Processing of Workflow Execution System]

Figure 15:
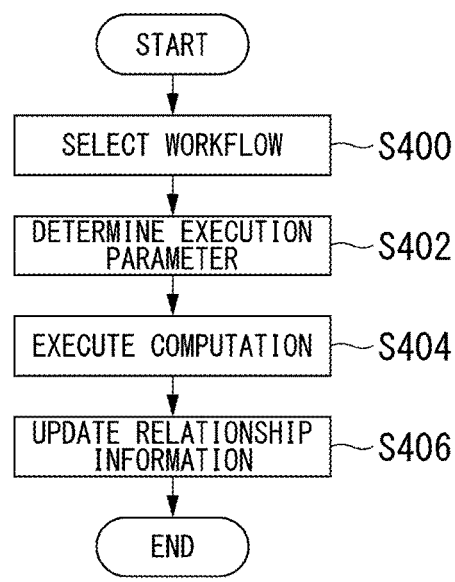
FIG. 15 is a flowchart showing an example of computation processing according to the present embodiment.

Next, an example of computation processing in the data storage method according to the present embodiment will be described with reference to FIG. 15. FIG. 15 is a flowchart showing an example of the computation processing according to the present embodiment.

First, after the above-described login process from the gateway, the user terminal 10 accepts an input by the system user for selecting the workflow execution system, and transmits the received information to the research and development support device 30. Based on the received information, the research and development support device 30 reads a program that executes the workflow execution system and transmits the program to the user terminal 10. Further, the research and development support device 30 transmits to the user terminal 10, information to select a workflow for executing computations, based on the received information (step S400).

The user terminal 10 accepts from the system user, an input for selecting the workflow for executing computations, and transmits the accepted information to the research and development support device 30. The research and development support device 30 receives the information and proceeds to the process in step S402.

Based on the acquired information, the research and development support device 30 reads the workflow and transmits to the user terminal 10, a page including information requesting inputs of parameters for executing computations. Here, the parameters for executing computations include input data based on the format of an input descriptor associated with an input port (hereinafter, also referred to as "execution parameters"), a description of a computation to be executed, and the like. The user terminal 10 displays the received page on the web browser. Subsequently, the user terminal 10 accepts from the system user, inputs of the parameters for executing the computation and an input instructing the execution of the computation, and transmits the information to the research and development support device 30 (step S402). The research and development support device 30 accepts the received information and proceeds to the process in step S404.

Here, the execution parameters may be a file described in advance in the descriptor format, or may be one inputted on the web browser. In this case, the user terminal 10 may convert the inputted execution parameters into the above file and transmit the file to the research and development support device 30. Further, the user terminal 10 may transmit the inputted execution parameters without performing the conversion. In this case, the research and development support device 30 converts the received execution parameters into the file described in the descriptor format.

Further, when performing computations on a plurality of patterns each having different execution parameters, the user terminal 10 may accept one in a file format including all the execution parameters of each of the plurality of patterns described in advance in the descriptor format. This is a case where, for example, many numerical values (N2, N3, . . . Nm) in the vicinity of a numerical value N1 of an execution parameter are calculated. Further, for example, the numerical value N1, the number m of numerical values in the vicinity to be calculated, and the interval (=N2−N1) between the numerical values may be specified on the web browser. In this case as well, as described above, a value inputted by the user terminal 10 or the research and development support device 30 is converted into a file described in the descriptor format.

Here, if the execution parameters are described in the descriptor format, the execution parameters are not limited to the file format. For example, data inputted in the descriptor format on the web browser may be accepted as execution parameters.

The research and development support device 30 executes the computation of the workflow based on the received parameter information (step S404). Further, when there are parameters of a plurality of patterns, the research and development support device 30 sequentially executes the computation the number of times corresponding to the number of those patterns. The research and development support device 30 causes the computation result storage unit 325 to store, as the execution date and time of the entire computation, the date and time when the information for executing the computation of the entire workflow is received. Here, if the research and development support device 30 cannot immediately execute the computation due to reasons such that the computation of another workflow is being executed, that computation is registered in a list in the computation waiting state, and a status indicating the computation result is set to "before start". When the computation becomes executable, the research and development support device 30 sequentially executes the computations of the execution programs in the order described in the workflow by using the execution programs corresponding to the prediction models included in the workflow. During the execution, the research and development support device 30 sets the status to "executing".

The research and development support device 30 causes the computation result storage unit 325 to store, for each execution program, the input and output data of the execution program, the read date and time (creation date and time), the computation start date and time, and the computation completion date and time of the execution program.

Further, when the computations of the entire workflow is completed, that is, the computations using the execution programs corresponding to all the prediction models included in the workflow has been completed, the research and development support device 30 causes the computation result storage unit 325 to store the date and time when the entire computations have been completed. Further, the research and development support device 30 stores in a predetermined directory, the results of the entire computations and the log data at the time of executing the computations. Further, the research and development support device 30 sets the status to "completed".

If the execution program in the middle of computation cannot complete the computation, the research and development support device 30 determines that the execution of the computation using the workflow has failed. The case where the computation cannot be completed is, for example, a case where the execution program causes an error during the computation for some reason, or a case where the execution program cannot complete the computation within a predetermined time. In this case, the research and development support device 30 may cancel the execution of all the computations of the other execution programs. Alternatively, the execution of the computation may be canceled only for the execution program that executes the computation using the output data of the execution program whose computation cannot be completed, and the execution of the computations may be continued for the other execution programs. The research and development support device 30 sets the status to "failure".

When the user terminal 10 accepts an input instructing cancellation of a computation is received while the computation is waiting for execution or is being executed, the user terminal 10 transmits the information to the research and development support device 30. Based on the received information, the research and development support device 30 performs a process of cancelling the waiting for execution of the computation or canceling the computation. In this case, the research and development support device 30 sets the status to "canceled".

If the research and development support device 30 completes, fails, or cancels the computation, the process proceeds to step S406.

When the research and development support device 30 cancels the computation, the research and development support device 30 ends the processing without performing anything.

When the research and development support device 30 completes, or fails in, the computation, the research and development support device 30 causes the relationship information storage unit 326 to store the information regarding the computation result (step S406), Thereafter, the research and development support device 30 ends the processing.

The user terminal 10 can display the computation status of the research and development support device 30 on the web browser, regardless of the execution status of the computation of the research and development support device 30.

FIG. 16 is a diagram showing an example of a computation list screen in the workflow execution system according to the present embodiment.

The user terminal 10 transmits to the research and development support device 30, information requesting information regarding a list of computations instructed to be executed (hereinafter, also referred to as a "run list"). Based on the received information, the research and development support device 30 reads the information regarding the computation list from the computation result storage unit 325 and transmits the information to the user terminal 10. Here, the information to be transmitted may be only the run list of the system user, or may be the run list of users included in the same group as the system user.

As shown in FIG. 16, based on the received information, the user terminal 10 displays a run list screen D50 on the web browser. The run list screen D50 includes information of the acquired run list, a check box CB51, a computation cancel button BT52, a computation information deletion button BT53, and the like.

The run list screen D50 displays the information of the acquired run list in a table format, for example, as shown in FIG. 16. The run list screen D50 displays, as information regarding each computation, for example, a run ID, a link L54 to a page displaying detailed information of the computation indicated by the run ID, a workflow name, an executor, an execution date and time, a status D55, a description, and the like. The run list screen D50 displays the status of the computation on the status D55 according to the progress of the computation.

In FIG. 16, the check box CB51 adjacent to the left side of the column displaying each computation is a check box for selecting an adjacent computation. The computation cancel button BT52 is a button for instructing to cancel the execution of the computation selected by the check box CBS1. Further, before the computation is executed, the computation cancel button BT52 is a button for instructing to cancel the execution of the computation. When the computation cancel button BT52 is pressed by the user, the user terminal 10 transmits to the research and development support device 30, information instructing the cancellation of the computation selected by the check box CB51. The research and development support device 30 cancels the execution of the computation based on the received information.

The computation information deletion button BT53 is a button for instructing deletion of the information regarding the computation selected by the check box CB51. The deletion of the information regarding the computation means, for example, the deletion of the information regarding the computation stored in the computation result storage unit 325, the deletion of the directory for storing the computation results, or the like. When the computation information deletion button BT53 is pressed by the user, the user terminal 10 transmits to the research and development support device 30, information instructing the deletion of the information regarding the computation selected by the check box CBS1. The research and development support device 30 deletes the information regarding the computation based on the received information.

Here, the user terminal 10 may disable the computation cancel button BT52 and the computation information deletion button BT53 when none of the check boxes CB51 is selected. Further, when only a computation for which the computation has been completed is selected in the check box CB51, the computation cancel button BT52 may be disabled.

FIG. 17 is a diagram showing an example of a computation detail screen in the workflow execution system according to the present embodiment.

The user terminal 10 transmits to the research and development support device 30, information requesting information regarding the details of the computation instructed to be executed (hereinafter, also referred to as "run details"). Based on the received information, the research and development support device 30 reads the information regarding the details of the computation from the computation result storage unit 325 and transmits the information to the user terminal 10.

As shown in FIG. 17, the user terminal 10 displays a run detail screen D60 on the web browser based on the received information. The run detail screen D60 includes information of the acquired run details, an execution status confirmation button BT61, a computation cancel button BT62, a computation information deletion button BT63, and the like.

The run detail screen D60 displays the information of the acquired run details, for example, as shown in FIG. 17.

The run detail screen D60 displays, as the information of the run details, information such as a run ID, a workflow name, a file name, an executor, a status, a description, an execution parameter, an execution date and time, a completion date and time, a computation job, an execution result, and a log. Here, the workflow name indicates information that identifies a workflow used to execute the computation. In FIG. 17, an alias of the workflow is displayed as the workflow name, but the example is not limited thereto. Further, the workflow name may include a link L64 for transmitting to the research and development support device 30, information requesting information for displaying the details regarding the workflow in the workflow design system. When the link L64 is selected by the system user, the user terminal 10 transmits to the research and development support device 30, information for displaying the workflow.

The file name indicates a file name of the workflow. The execution parameter indicates information regarding input data described in the format of an input descriptor when performing the computation.

The computation job displays information regarding the execution program. A button BT65 that can download data summarizing the computation results when the computations are completed is displayed at the execution result. Here, the downloading button may be displayed for each execution program. A link L66 for displaying or downloading the log at the time of the computation is displayed at the log.

The execution status confirmation button BT61 is a button for instructing the display of the run list screen D50 in FIG. 16. When the BT61 button is pressed by the system user, the user terminal 10 transmits to the research and development support device 30, information requesting information for displaying the run list screen D50.

The computation cancel button BT62 is a button for instructing to cancel the execution of the displayed computation. Further, before the computation is executed, the computation cancel button BT62 is a button for instructing to cancel the execution of the computation. When the computation cancel button BT62 is pressed by the user, the user terminal 10 transmits to the research and development support device 30, information instructing cancellation of the displayed computation. The research and development support device 30 cancels the execution of the computation based on the received information.

The computation information deletion button BT63 is a button for instructing deletion of information regarding the displayed computation. The deletion of the information regarding the computation means, for example, the deletion of the information regarding the computation stored in the computation result storage unit 325, the deletion of the directory for storing the computation result, or the like. When the computation information deletion button BT63 is pressed by the user, the user terminal 10 transmits to the research and development support device 30, information instructing the deletion of the displayed information regarding the computation. The research and development support device 30 deletes the information regarding the computation, based on the received information.

Here, when the computation has been completed, the user terminal 10 may not display or disable the computation cancel button BT62.

Here, when calculating a plurality of patterns each having different execution parameters, the computation execution unit 334 may include the best input value of the execution parameter in the computation result, based on the results of executing the computations. In this case, the computation execution unit 334 obtains a response curved surface based on the plurality of patterns and the computation results thereof, and obtains, based on the response curved surface, the best value of the execution parameter from the plurality of patterns each having different execution parameters. Further, when there are a plurality of outputs and the best execution parameter differs for each output, all the values of the execution parameters corresponding to the respective outputs may be included in the computation results.

As described above, in order to perform a model construction for executing performance prediction, property prediction, or structure prediction of a material, the prediction management system 1 according to the present embodiment describes in a plurality of hierarchical layers, information regarding the model construction which includes: descriptors each describing a parameter regarding at least one of processing means, a structure, a property, or a performance of the material; prediction models each describing a relationship between an input and an output in a first computation using one descriptor as the input and another descriptor as the output; a workflow describing that at least two of the prediction models are connected to each other via the input and output descriptor; and an execution result of a second computation executed using the workflow and execution parameters that are information for executing the second computation combining a plurality of the first computations included in the workflow. The prediction management system 1 includes: the inventory processing unit 3331 that registers the descriptors and the prediction models in the description format of this description; the workflow processing unit 3332 that designs the workflow using the prediction models registered in the inventory processing unit 3331; the computation execution unit 334 that sequentially executes the second computation using the workflow and the execution parameters; the descriptor storage unit 322 that is a descriptor database that stores the descriptors; the prediction model storage unit 323 that is a prediction model database for storing the prediction models; the workflow storage unit 324 that is a workflow database for storing the workflow; the computation result storage unit 325 that is a result database for storing the result of executing the second computation using the workflow; and the display unit 13.

As a result, the prediction management system 1 according to the present embodiment can, for example, visualize and accumulate the knowledge about the past material development. Further, the prediction management system 1 can visualize a model for predicting the properties of a material in a machine-readable format and share the model with a third party. Therefore, the prediction management system 1 according to the present embodiment can provide, for example, a general-purpose description, storage, and utilization method of information for realizing model construction, and enable the model construction for executing on a computer, the performance prediction, property prediction, and structure prediction of the material.

In the above-described embodiment, the inventory is changed after the inventory is displayed once, but the example is not limited thereto. For example, the user terminal 10 may display a screen for selecting the inventory to be changed, and transmit the information of the inventory to the research and development support device 30 when the system user selects the inventory to be changed. At this time, for example, the research and development support device 30 transmits to the user terminal 10, information for displaying the screen such as FIG. 10B or FIG. 12B. The user terminal 10 displays the received information on the web browser.

Further, the user information storage unit 327 may store information regarding the authority to browse and edit the description format group. Here, for example, the authority may be given to each group including a plurality of system users. Further, the authority to browse and the authority to edit may be given individually. Further, the storage unit of the description format group stores the authority to browse and edit the description format group. In this case, the system user can browse or edit only the description format group that can be browsed and edited with the system user's own authority.

Further, the workflow described in the above-described embodiment does not include a prediction model that outputs the performance, but the example is not limited thereto. Here, a workflow for predicting the creep life of heat-resistant steel including a welded portion will be described as an example.

Figure 18:
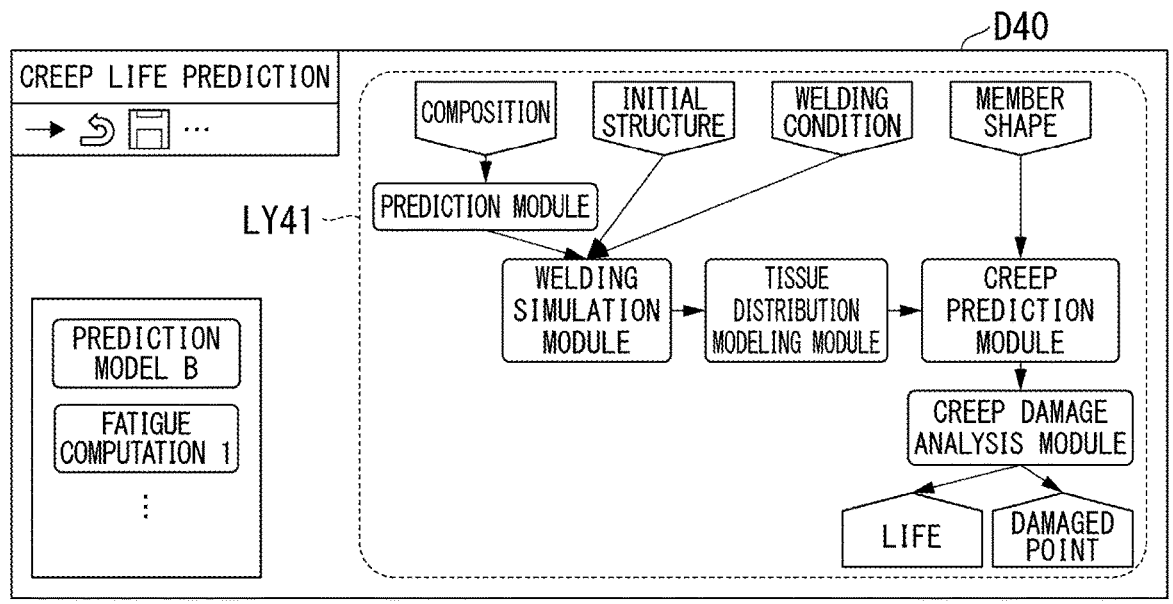
FIG. 18 is a diagram showing an example of a workflow design screen for predicting creep life in the workflow design system according to the present embodiment.

FIG. 18 is a diagram showing an example of a workflow design screen for predicting the creep life in the workflow design system.

The workflow display unit LY41 of FIG. 18 displays a workflow for predicting the creep life of the heat-resistant steel including the welded portion. In this workflow, an initial structure which is one of the structures, and a composition, a welding condition, and a member shape which are the processing means, are used as input descriptors of the entire workflow, while the life and a damaged point which are descriptors of performance, are used as output descriptions of the entire workflow. Here, the initial structure is a descriptor that describes information regarding the structure of the member before welding is performed. The composition is a descriptor that describes information regarding the composition of the member used for the welding. The welding condition is a descriptor that describes information regarding a welding condition. The member shape is a descriptor that describes information regarding the shape of the welded portion or the like of the member used for the welding. Further, the life is a descriptor that describes information regarding matters that contribute to the damage to the welded portion, such as the number of times the stress has been repeated until the damage to the welded portion occurs. The damaged point is a descriptor that describes information regarding the damaged point of the welded portion.

This workflow includes five prediction models identified by the names of a prediction module, a welding simulation module, a tissue distribution modeling module, a creep prediction module, and a creep damage analysis module. The prediction module accepts the composition as an input, and outputs continuous cooling property which is one of the properties. The welding simulation module is a model that accepts as inputs, the initial structure, the welding condition, and the continuous cooling property, and outputs a welding microstructure which is one of the structures, and the corresponding execution program is a program that imitates welding. The tissue distribution modeling module is a model that accepts the weld microstructure as an input and outputs a heat-affected zone coarse-grained structure which is one of the structures, and the corresponding execution program models a structure distribution and coarse grains a heat-affected zone affected by heat during the welding. The creep prediction module is a model that accepts the heat-affected zone coarse-grained structure and the member shape as inputs, and outputs a welded portion creep property which is one of the properties, and the corresponding execution program is the execution program of a database regarding creep prediction. The creep damage analysis module is a model that accepts the welded portion creep property as an input and outputs the life and the damaged point, and the corresponding execution program analyzes the creep damage. Thus, by freely combining the four types of inputs and outputs which are the processing means, the structure, the property, and the performance, more complicated performance prediction, property prediction, and structure prediction of materials can be performed.

Further, a workflow WF1 may be used as part of the design of another workflow WF2. In this case, for example, information regarding the input and output of the workflow WF1 may be stored in the prediction model storage unit 323 as a new prediction model. At this time, a plurality of execution programs included in the workflow WF1 are combined into one and stored in the prediction model storage unit 323 as an execution program corresponding to the new prediction model. The prediction model palette display unit P42 may also display another workflow as a figure with an identifiable expression, as in the prediction model. Further, the identification information displayed on the figure showing the inventory, the workflow, or the like, which is displayed on the workflow design screen D40, may include link information to a screen displaying the detailed information of the inventory, link information to a screen displaying the workflow, or the like.

Further, in the workflow computation, when a computation is performed for many points in the vicinity of a certain numerical value at once, an API for giving the instruction may be stored in the web application program storage unit 321, so that the computation for the neighborhood points can be performed using this. In this case, the system user can easily perform the computation for a large number of neighborhood points without preparing data for the computation of the neighborhood points in advance.

Here, one aspect of the present invention is not limited to the above embodiment, and can be changed without departing from the spirit of the present invention.

For example, in the above embodiment, the description has been given with respect to the example where the management terminal 20 and the research and development support device 30 are configured as individual devices, but the example is not limited thereto, and the management terminal 20 and the research and development support device 30 may be configured as one device. Further, for example, the research and development support device 30 may be configured as two devices, which are a model design device and a computation execution device. Further, for example, a device that performs processing regarding the web application program may be configured as a device different from the research and development support device 30.

Further, in the above embodiment, the example in which the research and development support device 30 includes the storage unit 32 has been described, but a part or all of the storage unit 32 may be provided outside the research and development support device 30.

Further, a part of the research and development support device 30 in the above-described embodiment, for example, the processing unit 33 or the like, may be realized by a computer. In that case, this may be realized by recording a program for realizing this function on a computer-readable recording medium, and causing a computer system to read and execute the program recorded on the recording medium. Here, the "computer system" referred hereto is a computer system built in the research and development support device 30, and includes hardware such as an OS (Operating System) and peripheral devices.

Further, the "computer-readable recording medium" refers to a portable medium such as a flexible disk, a magneto-optical disk, a ROM, or a CD-ROM, or a storage device such as a hard disk built in a computer system. Furthermore, a "computer-readable recording medium" may include: a computer-readable recording medium that dynamically holds a program for a short period of time, such as a communication line when a program is transmitted via a network such as the Internet or a communication line such as a telephone line; and a computer-readable recording medium that holds a program for a certain period of time, such as a volatile memory inside a computer system serving as a server or a client in that case. Further, the above-described program may be a program for realizing a part of the above-described functions, and may be a program that can realize the above-described functions in combination with a program already recorded in the computer system.

Although one embodiment of the present invention has been described above in detail with reference to the drawings, the specific configuration is not limited to the above, and various design changes and the like can be made without departing from the gist of the present invention.

INDUSTRIAL APPLICABILITY

One aspect of the present invention can be used, for example, in a computer system that makes predictions regarding materials, or in developments or researches of substances or materials.

DESCRIPTION OF REFERENCE NUMERALS

1 . . . prediction management system
10 . . . user terminal
11, 21, 31 . . . communication unit
12, 22 . . . input unit
13, 23 . . . display unit
14, 24, 32 . . . storage unit
15, 25, 33 . . . processing unit
20 . . . management terminal
30 . . . research and development support device
321 . . . web application program storage
322 . . . descriptor storage unit
323 . . . prediction model storage unit
324 . . . workflow storage unit
325 . . . computation result storage unit
326 . . . relationship information storage unit
327 . . . user information storage unit
331 . . . acquisition unit
332 . . . API processing unit
333 . . . model processing unit
3331 . . . inventory processing unit
3332 . . . workflow processing unit
334 . . . computation execution unit 335 . . . user information processing unit
336 . . . output unit
NW . . . network NW

The invention claimed is:

1. A prediction management system that makes a prediction regarding a material, the prediction management system comprising:
a processor; and
a non-transitory memory storing instructions that, when executed by the processor, cause the processor to perform operations comprising:
storing descriptors in a descriptor storage, each descriptor of the descriptors describing a parameter regarding processing means, a structure, a property, or a performance of the material;
storing prediction models in a prediction model storage, each prediction model of the prediction models describing an input and output relationship among the descriptors, wherein each prediction model accepts, as an input descriptor, one of at least two of the processing means, the structure, the property, and the performance, and outputs another one thereof as an output descriptor;
storing workflows in a workflow storage, each workflow of the workflows describing that at least two of the prediction models are connected to each other via a descriptor, wherein the output descriptor of one prediction model is accepted as the input descriptor of another prediction model;
giving an input to each workflow of the workflows, executing the workflow including execution of each prediction model included in the workflow, and storing an execution result including an output result of each prediction model included in the workflow indicating the prediction regarding the material; and
managing execution results, the workflows, the prediction models, and the descriptors in four hierarchical layers by assigning a unique identifier.

2. The prediction management system according to claim 1, wherein the operations further comprise:
registering the descriptors and the prediction models;
generating images representing the prediction models as registered and designing the workflows based on a user operation of connecting a plurality of the images of the prediction models to one another;
managing the workflows so as to be available to a plurality of users; and
causing the execution result of the workflow to be stored, including identification information of a user who executed the workflow.

3. The prediction management system according to claim 1, wherein the operations comprise:
describing the input and output relationship among the descriptors as a plurality of types of inputs or outputs among the processing means, the structure, the property, and the performance; and
giving an input to, and executing, the workflow including execution of the prediction model describing the input and output relationship as the plurality of types of inputs or outputs.

4. The prediction management system according to claim 1, wherein the operations comprise:
describing the input and output relationship among the descriptors of at least one of the prediction models so as to accept the processing means and the structure as inputs and output the property; and
giving an input to, and executing, the workflow including the prediction model describing the input and output relationship so as to accept the processing means and the structure as inputs and output the property.

5. The prediction management system according to claim 1, wherein the operations comprise:
describing the input and output relationship among the descriptors of at least one of the prediction models so as to accept the processing means and the structure as inputs and output the structure; and
giving an input to, and executing, the workflow including the prediction model describing the input and output relationship so as to accept the processing means and the structure as inputs and output the structure.

6. A prediction management method in a prediction management system that makes a prediction regarding a material, the prediction management method comprising:
storing descriptors in a descriptor storage, each descriptor of the descriptors describing a parameter regarding processing means, a structure, a property, or a performance of the material;
storing prediction models in a prediction model storage, each prediction model of the prediction models describing an input and output relationship among the descriptors, wherein each prediction model accepts, as an input descriptor, one of at least two of the processing means, the structure, the property, and the performance, and outputs another one thereof as an output descriptor;
storing workflows in a workflow storage, each workflow of the workflows describing that at least two of the prediction models are connected to each other via a descriptor, wherein the output descriptor of one prediction model is accepted as the input descriptor of another prediction model;
giving an input to each workflow of the workflows, executing the workflow including execution of each prediction model included in the workflow, and storing an execution result including an output result of each prediction model included in the workflow indicating the prediction regarding the material; and
managing the execution results, the workflows, the prediction models, and the descriptors in four hierarchical layers by assigning a unique identifier.

7. The prediction management method according to claim 6, wherein the method further comprises:
registering the descriptors and the prediction models;
generating images representing the prediction models as registered and designing the workflows based on a user operation of connecting a plurality of the images of the prediction models to one another;
managing the workflows so as to be available to a plurality of users; and
causing the execution result of the workflow to be stored, including identification information of a user who executed the workflow.

8. The prediction management method according to claim 6, wherein the method comprises:
describing the input and output relationship among the descriptors as a plurality of types of inputs or outputs among the processing means, the structure, the property, and the performance; and
giving an input to, and executing, the workflow including the prediction model describing the input and output relationship as the plurality of types of inputs or outputs.

9. The prediction management method according to claim 6, wherein the method comprises:

describing the input and output relationship among the descriptors of at least one of the prediction models so as to accept the processing means and the structure as inputs and output the property; and giving an input to, and executing, the workflow including the prediction model describing the input and output relationship so as to accept the processing means and the structure as inputs and output the property.

10. The prediction management method according to claim 6, wherein the method comprises:

describing the input and output relationship among the descriptors of at least one of the prediction models so as to accept the processing means and the structure as inputs and output the structure; and giving an input to, and executing, the workflow including the prediction model describing the input and output relationship so as to accept the processing means and the structure as inputs and output the structure.

* * * * *